US009994653B2

(12) United States Patent
Lee et al.

(10) Patent No.: US 9,994,653 B2
(45) Date of Patent: Jun. 12, 2018

(54) METALLOCENE COMPOUND, CATALYST COMPOSITION INCLUDING THE SAME, AND METHOD OF PREPARING OLEFIN-BASED POLYMER USING THE SAME

(71) Applicant: LG CHEM, LTD., Seoul (KR)

(72) Inventors: Yong Ho Lee, Daejeon (KR); Kyung Jin Cho, Daejeon (KR); Jin Young Park, Daejeon (KR); Ki Soo Lee, Daejeon (KR); Min Seok Cho, Daejeon (KR); Se Young Kim, Daejeon (KR); Sung Min Lee, Daejeon (KR); Chang Woan Han, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days. days.

(21) Appl. No.: 15/317,038

(22) PCT Filed: Jan. 28, 2015

(86) PCT No.: PCT/KR2015/000923
§ 371 (c)(1),
(2) Date: Dec. 7, 2016

(87) PCT Pub. No.: WO2016/122017
PCT Pub. Date: Aug. 4, 2016

(65) Prior Publication Data
US 2017/0137545 A1    May 18, 2017

(51) Int. Cl.
*C08F 4/6592* (2006.01)
*C08F 10/00* (2006.01)
*C07F 17/00* (2006.01)
*C08F 10/02* (2006.01)
*C08F 4/659* (2006.01)

(52) U.S. Cl.
CPC .............. *C08F 10/02* (2013.01); *C07F 17/00* (2013.01); *C08F 4/65908* (2013.01); *C08F 4/65912* (2013.01); *C08F 4/65927* (2013.01)

(58) Field of Classification Search
CPC .............. C08F 4/65927; C08F 4/65908; C08F 210/16; C08F 10/00
See application file for complete search history.

(56) References Cited

U.S. PATENT DOCUMENTS

| 5,064,802 A | 11/1991 | Stevens et al. |
| 6,683,150 B1 | 1/2004 | Meverden et al. |
| 6,756,455 B2 | 6/2004 | Nagy et al. |
| 6,908,972 B2 | 6/2005 | Tsuie et al. |
| 7,655,740 B2 | 2/2010 | Nagy et al. |
| 7,723,451 B2 | 5/2010 | Nagy et al. |
| 8,124,557 B2 | 2/2012 | Lee et al. |
| 2009/0062488 A1 | 3/2009 | Nagy et al. |
| 2012/0123078 A1 | 5/2012 | Lee et al. |
| 2013/0296497 A1* | 11/2013 | Jeong ............... C08F 297/08 525/321 |
| 2016/0159828 A1 | 6/2016 | Lee et al. |
| 2016/0168281 A1 | 6/2016 | Lee et al. |

FOREIGN PATENT DOCUMENTS

| KR | 10-2004-0085650 A | 10/2004 |
| KR | 10-2011-0130839 A | 12/2011 |
| KR | 101154507 B1 | 6/2012 |
| KR | 10-2012-087706 A | 8/2012 |
| KR | 10-2015-0037520 A | 4/2015 |
| KR | 10-2015-0057964 A | 5/2015 |
| WO | 99/24446 A1 | 5/1999 |
| WO | 2009/032049 A1 | 3/2009 |

* cited by examiner

*Primary Examiner* — Caixia Lu
(74) *Attorney, Agent, or Firm* — Dentons US LLP

(57) ABSTRACT

Provided are a novel metallocene compound, a catalyst composition including the same, and a method of preparing an olefin-based polymer using the same. The metallocene compound according to the present invention or the catalyst composition including the same may be used for the preparation of an olefin-based polymer, may have excellent polymerization ability, and may produce an olefin-based polymer having a high molecular weight. In particular, when the metallocene compound according to the present invention is employed, an olefin-based polymer having a high molecular weight may be polymerized because the metallocene compound shows high polymerization activity even when it is supported on a support and maintains high activity even in the presence of hydrogen because of its low hydrogen reactivity.

14 Claims, No Drawings

METALLOCENE COMPOUND, CATALYST COMPOSITION INCLUDING THE SAME, AND METHOD OF PREPARING OLEFIN-BASED POLYMER USING THE SAME

This application is a National Stage Entry of International Application No. PCT/KR2015/000923, filed Jan. 28, 2015, all of which are hereby incorporated by reference in its entirety for all purposes as if fully set forth herein.

TECHNICAL FIELD

The present disclosure relates to a novel metallocene compound, a catalyst composition including the same, and a method of preparing an olefin-based polymer using the same.

BACKGROUND OF THE INVENTION

In the early 1990s, [Me$_2$Si(Me$_4$C$_5$)NtBu]TiCl$_2$ (Constrained-Geometry Catalyst, hereinafter abbreviated as CGC) was reported by Dow Co. (U.S. Pat. No. 5,064,802), and superior aspects of the CGC in a copolymerization reaction of ethylene and alpha-olefin may be summarized by the following two points when compared to commonly known metallocene catalysts. (1) At a high polymerization temperature, high activity is shown and a polymer having a high molecular weight is produced, and (2) the copolymerization ability of alpha-olefin having large steric hindrance such as 1-hexene and 1-octene is excellent. In addition, a variety of characteristics of CGC upon polymerization are gradually becoming known, and thus thorough research into synthesis of derivatives thereof to serve as a polymerization catalyst is ongoing in academic and industrial fields.

A Group 4 transition metal compound having one or two cyclopentadienyl groups as a ligand may be used as a catalyst for olefin polymerization by activating it with methylaluminoxane or a boron compound. Such catalyst shows unique characteristics that a traditional Zeigler-Natta catalyst cannot realize.

That is, a polymer obtained by using such catalyst has a narrow molecular weight distribution and higher reactivity for a second monomer such as alpha-olefin or cycloolefin, and distribution of the second monomer in the polymer is even. Furthermore, it is possible to control the stereoselectivity of the polymer in the polymerization of alpha-olefin by changing the substituent of the cyclopentadienyl ligand in the metallocene catalyst, and it is easy to control the degree of copolymerization, the molecular weight, and the distribution of the second monomer upon copolymerization of ethylene and other olefins.

Meanwhile, since the metallocene catalyst is more expensive than the Zeigler-Natta catalyst, it must have good activity for its economic cost. If the metallocene catalyst has high reactivity for the second monomer, there is an advantage that a polymer including a large amount of the second monomer may be obtained by using only a small amount of the second monomer.

Many researchers have studied various catalysts, and as a result, it is proven that a bridged catalyst generally has high reactivity for the second monomer. The bridged catalysts developed until now may be classified into three types according the type of the bridge. One is a catalyst of which two cyclopentadienyl ligands are connected with an alkylene dibridge by the reaction of an electrophile such as an alkyl halide and indene or fluorene, another is a silicone-bridged catalyst of which the ligands are connected with —SiR$_2$—, and the other is a methylene-bridged catalyst which is obtained by the reaction of fulvene and indene or fluorene.

Among the above attempts, however, very few catalysts have been practically applied in commercial factories, and thus preparation of catalysts showing more improved polymerization performance is still required.

DETAIL OF THE INVENTION

Objectives of the Invention

In order to solve the problems of the prior art, the present invention provides a metallocene compound having excellent activity and that is capable of producing an olefin-based polymer having a high molecular weight, a catalyst composition including the same, a method of preparing an olefin-based polymer using the same, and an olefin-based polymer prepared by using the same.

Particularly, the present invention provides a metallocene compound which shows high polymerization activity even when it is supported on a support, maintains high activity even in the presence of hydrogen because of its low hydrogen reactivity, and is able to polymerize an olefin-based polymer having a high molecular weight, a catalyst composition including the same, a method of preparing an olefin-based polymer using the same, and an olefin-based polymer prepared by using the same.

Means for Achieving the Objective

The present invention provides a metallocene compound represented by the following Chemical Formula 1:

[Chemical Formula 1]

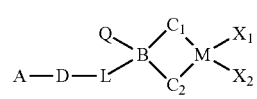

wherein A is hydrogen, a halogen, a C1 to C20 alkyl group, a C2 to C20 alkenyl group, a C6 to C20 aryl group, a C7 to C20 alkylaryl group, a C7 to C20 arylalkyl group, a C1 to C20 alkoxy group, a C2 to C20 alkoxyalkyl group, a C3 to C20 heterocycloalkyl group, or a C5 to C20 heteroaryl group;

D is —O—, —S—, —N(R)—, or —Si(R)(R')—, wherein R and R' are the same as or different from each other, and are each independently hydrogen, a halogen, a C1 to C20 alkyl group, a C2 to C20 alkenyl group, or a C6 to C20 aryl group;

L is a C1 to C10 linear or branched alkylene group;

B is carbon, silicon, or germanium;

Q is hydrogen, a halogen, a C1 to C20 alkyl group, a C2 to C20 alkenyl group, a C6 to C20 aryl group, a C7 to C20 alkylaryl group, or a C7 to C20 arylalkyl group;

M is a Group 4 transition metal;

$X_1$ and $X_2$ are the same as or different from each other, and are each independently a halogen, a C1 to C20 alkyl group, a C2 to C20 alkenyl group, a C6 to C20 aryl group, a nitro group, an amido group, a C1 to C20 alkylsilyl group, a C1 to C20 alkoxy group, or a C1 to C20 sulfonate group; and $C_1$ and $C_2$ are the same as or different from each other, and at least one of $C_1$ and $C_2$ is represented by the following Chemical Formula 2, and the other is cyclopentadienyl, indenyl, 4,5,6,7-tetrahydro-1-indenyl, fluorenyl, or indenoindolyl, and they may be substituted with a C1 to C20 alkyl group, a C3 to C20 cycloalkyl group, a C6 to C20 aryl group, a C7 to C20 alkylaryl group, or a C7 to C20 arylalkyl group,

[Chemical Formula 2]

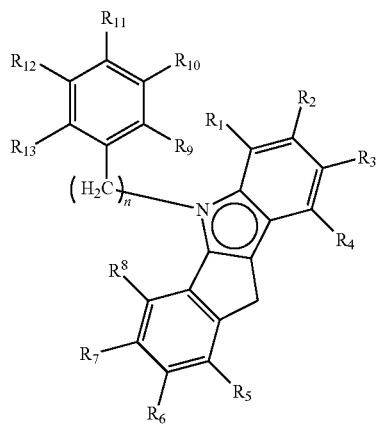

wherein n is an integer of 0 to 5; and $R_1$ to $R_{13}$ are the same as or different from each other, and are each independently hydrogen, a halogen, a C1 to C20 alkyl group, a C2 to C20 alkenyl group, a C1 to C20 alkylsilyl group, a C1 to C20 silylalkyl group, a C1 to C20 alkoxysilyl group, a C1 to C20 alkoxy group, a C6 to C20 aryl group, a C7 to C20 alkylaryl group, or a C7 to C20 arylalkyl group, and at least one of $R_9$ to $R_{13}$ is a halogen.

Further, the present invention provides a catalyst composition including the metallocene compound.

The present invention also provides a method of preparing an olefin-based polymer, including the step of polymerizing olefin-based monomers in the presence of the catalyst composition.

In addition, the present invention provides an olefin-based polymer prepared by the preparation method.

Effects of the Invention

A metallocene compound according to the present invention or a catalyst composition including the same may be used for the preparation of an olefin-based polymer, may have excellent activity and copolymerization ability, and may produce an olefin-based polymer having a high molecular weight and a wide molecular weight distribution.

In particular, when the metallocene compound according to the present invention is employed, an olefin-based polymer having a high molecular weight may be polymerized because the metallocene compound shows high polymerization activity even when it is supported on a support and maintains high activity even in the presence of hydrogen because of its low hydrogen reactivity.

Furthermore, the activity of the catalyst may be maintained for a long residence time in a reactor because of its long lifetime.

DESCRIPTION OF THE EMBODIMENTS

In the present invention, the terms "first", "second", and the like are used to describe a variety of components, and these terms are merely employed to differentiate a certain component from other components.

Further, the terms used in this description are just for explaining exemplary embodiments, and are not intended to restrict the present invention. The singular expression may include the plural expression unless it is differently expressed contextually. It must be understood that the term "include", "equip", or "have" in the present description is only used for designating the existence of characteristics taking effect, numbers, steps, components, or combinations thereof, and do not exclude the existence or the possibility of addition of one or more different characteristics, numbers, steps, components of combinations thereof beforehand.

The present invention may be variously modified and have various forms, and specific examples of the present invention are explained in this description. However, it is not intended to limit the present invention to the specific examples, and it must be understood that the present invention includes all modifications, equivalents, or replacements included in the spirit and technical scope of the present invention.

Hereinafter, the present invention will be described in more detail.

A metallocene compound according to the present invention is characterized in that it is represented by the following Chemical Formula 1:

[Chemical Formula 1]

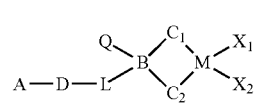

wherein A is hydrogen, a halogen, a C1 to C20 alkyl group, a C2 to C20 alkenyl group, a C6 to C20 aryl group, a C7 to C20 alkylaryl group, a C7 to C20 arylalkyl group, a C1 to C20 alkoxy group, a C2 to C20 alkoxyalkyl group, a C3 to C20 heterocycloalkyl group, or a C5 to C20 heteroaryl group;

D is —O—, —S—, —N(R)—, or —Si(R)(R')—, wherein R and R' are the same as or different from each other, and are each independently hydrogen, a halogen, a 01 to C20 alkyl group, a C2 to C20 alkenyl group, or a C6 to C20 aryl group;

L is a C1 to C10 linear or branched alkylene group;

B is carbon, silicon, or germanium;

Q is hydrogen, a halogen, a C1 to C20 alkyl group, a C2 to C20 alkenyl group, a C6 to C20 aryl group, a C7 to C20 alkylaryl group, or a C7 to C20 arylalkyl group;

M is a Group 4 transition metal;

$X_1$ and $X_2$ are the same as or different from each other, and are each independently a halogen, a C1 to C20 alkyl group, a C2 to C20 alkenyl group, a C6 to C20 aryl group, a nitro group, an amido group, a C1 to C20 alkylsilyl group, a C1 to C20 alkoxy group, or a C1 to C20 sulfonate group; and $C_1$ and $C_2$ are the same as or different from each other, and at least one of $C_1$ and $C_2$ is represented by the following Chemical Formula 2, and the other is cyclopentadienyl, indenyl, 4,5,6,7-tetrahydro-1-indenyl, fluorenyl, or indenoindolyl, and they may be substituted with a C1 to C20 alkyl group, a C3 to C20 cycloalkyl group, a C6 to C20 aryl group, a C7 to C20 alkylaryl group, or a C7 to C20 arylalkyl group,

[Chemical Formula 2]

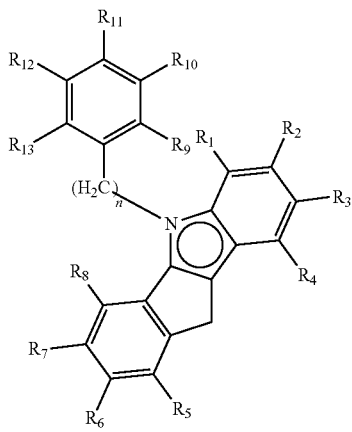

wherein n is an integer of 0 to 5; and $R_1$ to $R_{13}$ are the same as or different from each other, and are each independently hydrogen, a halogen, a C1 to C20 alkyl group, a C2 to C20 alkenyl group, a C1 to C20 alkylsilyl group, a C1 to C20 silylalkyl group, a C1 to C20 alkoxysilyl group, a C1 to C20 alkoxy group, a C6 to C20 aryl group, a C7 to C20 alkylaryl group, or a C7 to C20 arylalkyl group, and at least one of $R_9$ to $R_{13}$ is a halogen.

In the metallocene compound according to the present invention, the substituents of Chemical Formula 1 are more specifically explained as follows.

The C1 to C20 alkyl group may include a linear or branched alkyl group, and specifically, it may be a methyl group, an ethyl group, a propyl group, an isopropyl group, an n-butyl group, a tert-butyl group, a pentyl group, a hexyl group, a heptyl group, an octyl group, or the like, but is not limited thereto.

The C2 to C20 alkenyl group may include a linear or branched alkenyl group, and specifically, it may be an allyl group, an ethenyl group, a propenyl group, a butenyl group, a pentenyl group, or the like, but is not limited thereto.

The C6 to C20 aryl group may include a single ring aryl group or a condensed ring aryl group, and specifically, it may be a phenyl group, a biphenyl group, a naphthyl group, a phenanthrenyl group, a fluorenyl group, or the like, but is not limited thereto.

The C5 to C20 heteroaryl group may include a single ring heteroaryl group or a condensed ring heteroaryl group, and specifically, it may be a carbazolyl group, a pyridyl group, a quinoline group, an isoquinoline group, a thiophenyl group, a furanyl group, an imidazole group, an oxazolyl group, a thiazolyl group, a triazine group, a tetrahydropyranyl group, a tetrahydrofuranyl group, or the like, but is not limited thereto.

The C1 to C20 alkoxy group may be a methoxy group, an ethoxy group, a phenyloxy group, a cyclohexyloxy group, or the like, but is not limited thereto.

The Group 4 transition metal may be titanium, zirconium, hafnium, or the like, but is not limited thereto.

In the metallocene compound according to the present invention, it is more preferable that $R_1$ to $R_{13}$ in Chemical Formula 2 are each independently hydrogen, a halogen, a methyl group, an ethyl group, a propyl group, an isopropyl group, an n-butyl group, a tert-butyl group, a pentyl group, a hexyl group, a heptyl group, an octyl group, a phenyl group, a halogen group, a trimethylsilyl group, a triethylsilyl group, a tripropylsilyl group, a tributylsilyl group, a triisopropylsilyl group, a trimethylsilylmethyl group, a methoxy group, an ethoxy group, or the like, but is not limited thereto.

Further, it is preferable that at least one of $R_9$ to $R_{13}$ in Chemical Formula 2 is a halogen, and in particular, fluorine (F) among halogens. Additionally, it is more preferable that one or more, or two or more, of $R_9$ to $R_{13}$ in Chemical Formula 2 are halogens. When at least one of $R_9$ to $R_{13}$ is fluorine, beta-hydrogen of a polymer chain is stabilized by hydrogen bonding to further improve the effect of inhibiting beta-hydrogen elimination.

In Chemical Formula 2, n may be an integer of 0 to 5, and preferably 1 to 5.

In the metallocene compound according to the present invention, it is more preferable that L in Chemical Formula 1 is a C4 to C8 linear or branched alkylene group, but is not limited thereto. Furthermore, the alkylene group may be unsubstituted or substituted with a C1 to C20 alkyl group, a C2 to C20 alkenyl group, or a C6 to C20 aryl group.

In the metallocene compound according to the present invention, it is preferable that A in Chemical Formula 1 is hydrogen, a methyl group, an ethyl group, a propyl group, an isopropyl group, an n-butyl group, a tert-butyl group, a methoxymethyl group, a tert-butoxymethyl group, a 1-ethoxyethyl group, a 1-methyl-1-methoxyethyl group, a tetrahydropyranyl group, or a tetrahydrofuranyl group, but is not limited thereto.

In the metallocene compound according to the present invention, B in Chemical Formula 1 is preferably silicon, but is not limited thereto.

Since the metallocene compound of Chemical Formula 1 forms a structure in which an indenoindole derivative and a cyclopentadiene derivative are crosslinked by a bridge, and has an unshared electron pair acting as a Lewis base in the ligand structure, the metallocene compound may show high polymerization activity even when it is supported on the surface of a support having a Lewis acid characteristic. The nitrogen atom of the electron-rich indenoindole derivative stabilizes the beta-hydrogen of a growing polymer chain by hydrogen bonding and inhibits beta-hydrogen elimination, thereby polymerizing an olefin-based polymer having a high molecular weight. Further, the cyclopentadiene derivative with relatively low steric hindrance is included to show high copolymerization activity and low hydrogen reactivity, thereby polymerizing an olefin polymer having a high molecular weight with high activity. Furthermore, a substituent containing a halogen atom with excellent hydrogen binding ability is introduced to improve the effect of inhibiting the beta-hydrogen elimination. Additionally, the halogen atom may form a Lewis acid-base complex with a cocatalyst including aluminium (Al) to contribute to stabilization of a cation-anion pair of the activated catalyst.

According to an embodiment of the present invention, a specific example of the compound represented by Chemical Formula 2 may be a compound represented by any one of the following structural formulae, but is not limited thereto.

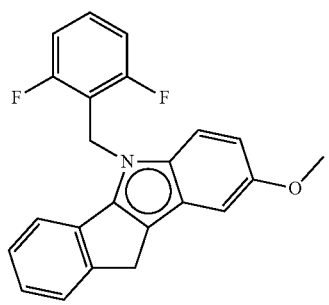

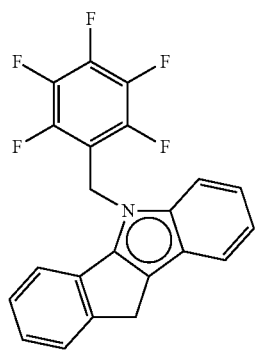 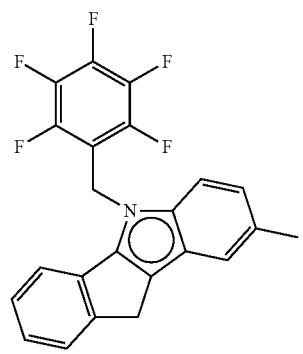

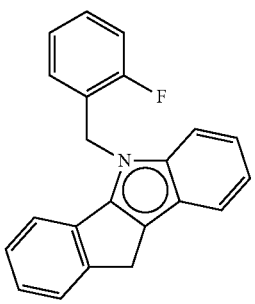 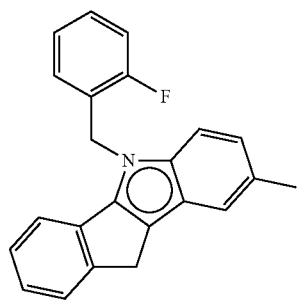

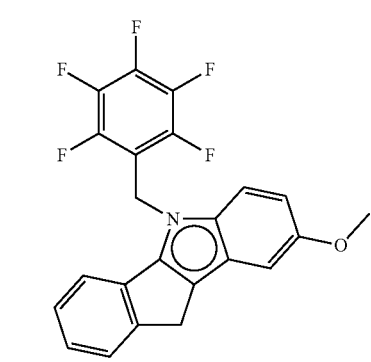

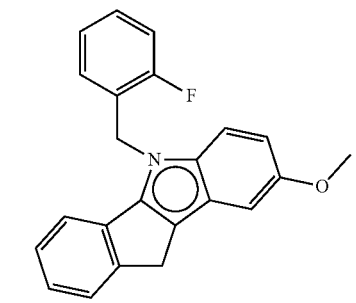

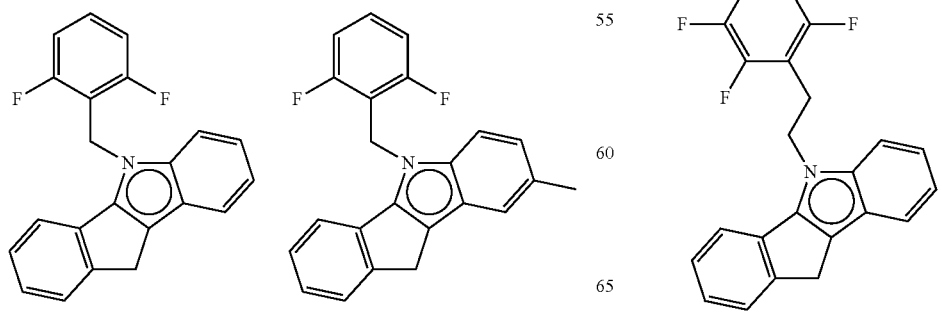

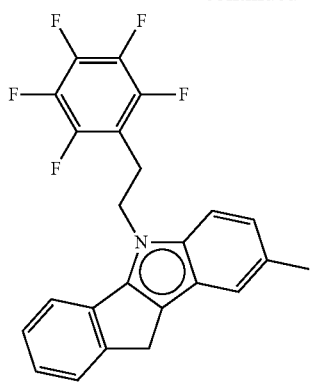
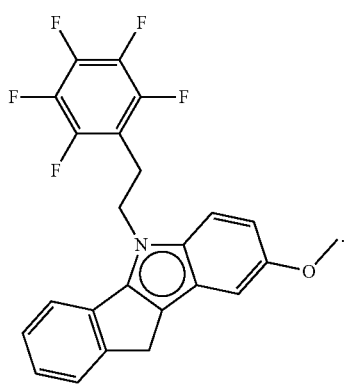
According to an embodiment of the present invention, a specific example of the metallocene compound of the present invention represented by Chemical Formula 1 may be a compound represented by any one of the following structural formulae, but is not limited thereto.
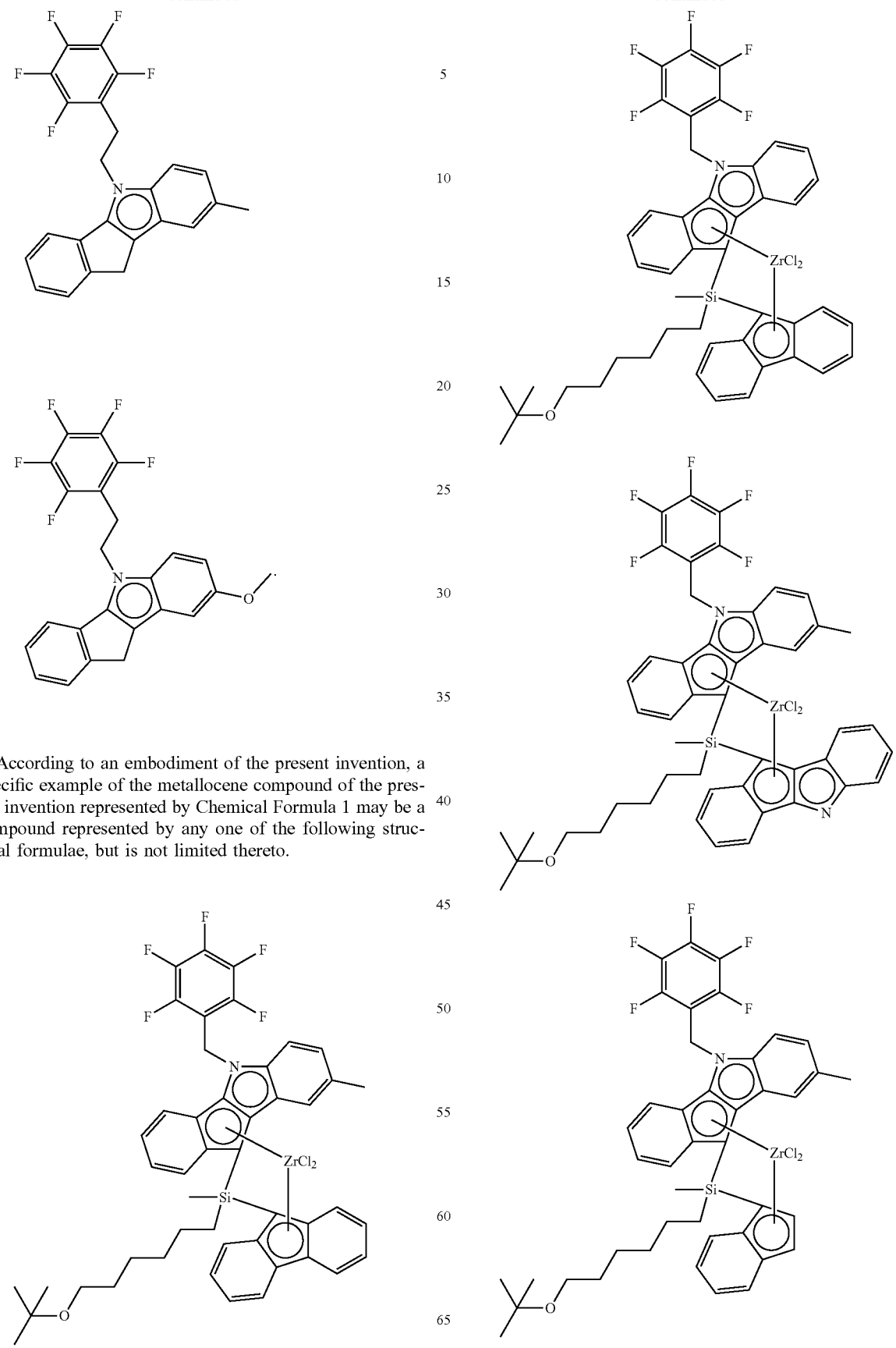

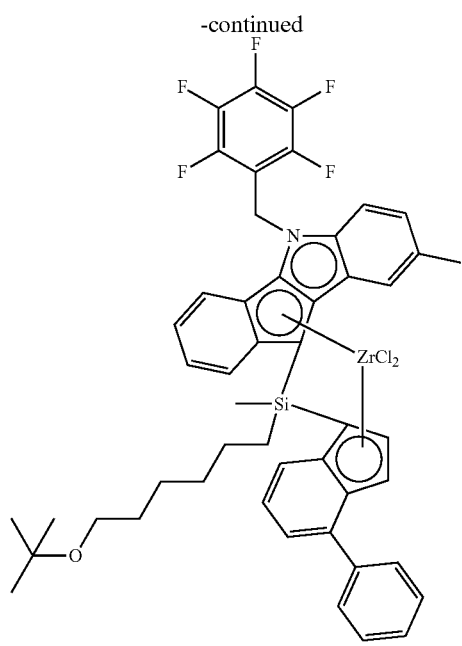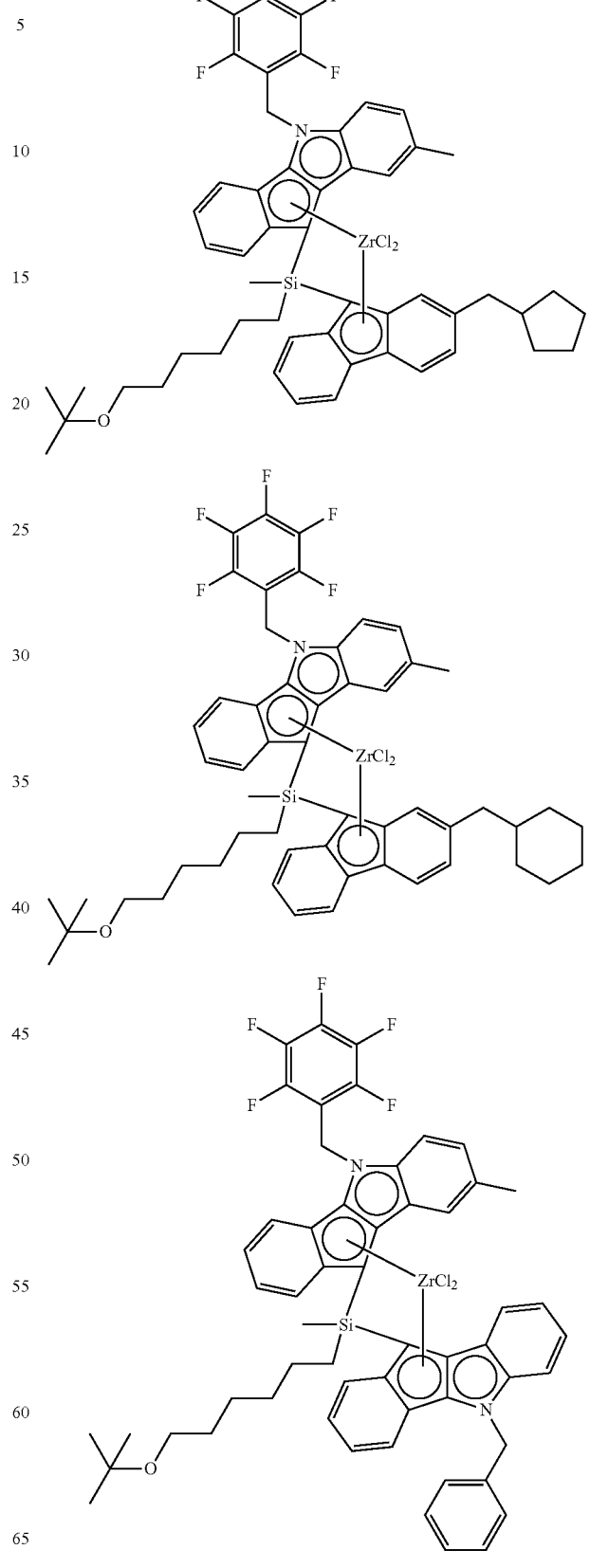

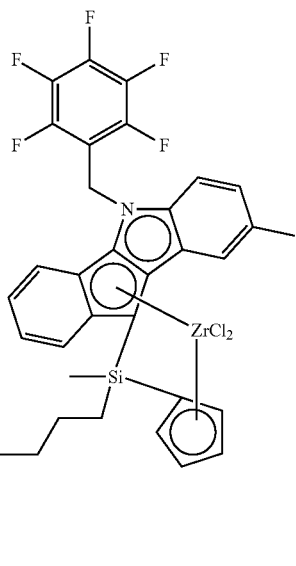
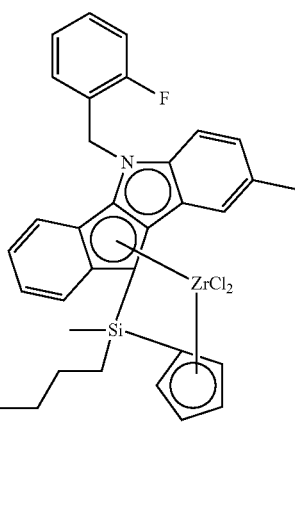
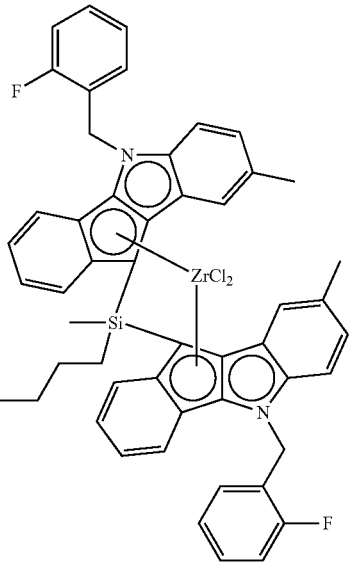
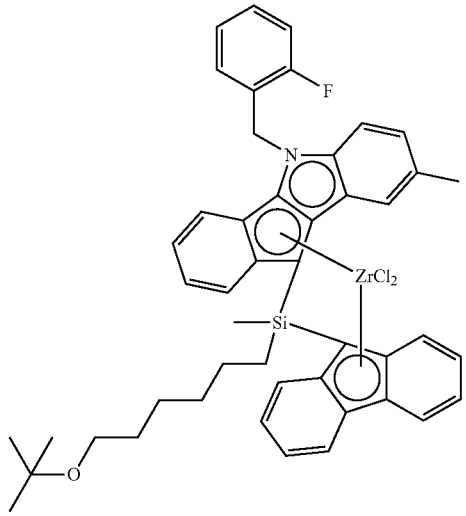
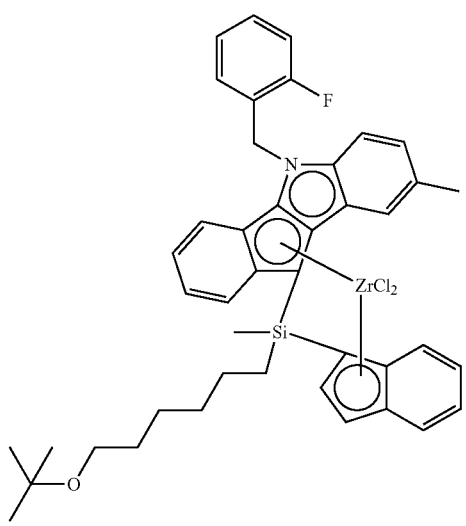
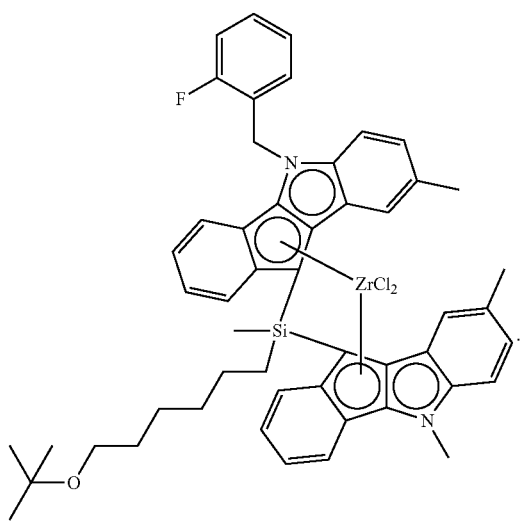

The metallocene compound according to the present invention may have excellent activity and may polymerize an olefin-based polymer having a high molecular weight. In particular, the metallocene compound may exhibit high polymerization activity when it is used in the form of being supported on a support. Therefore, the metallocene compound may prepare an olefin-based polymer having a high molecular weight even when it is used as a supported catalyst.

Furthermore, the metallocene compound according to the present invention may polymerize an olefin-based polymer having a high molecular weight while still having high activity because of its low hydrogen reactivity, even when the polymerization reaction is carried out in the presence of hydrogen in order to prepare an olefin-based polymer having a high molecular weight and a wide molecular weight distribution at the same time. Therefore, the metallocene compound may prepare an olefin-based polymer satisfying the high molecular characteristic without a decrease in activity even when the metallocene compound is heterogeneously used together with a catalyst having different characteristics, and thus the olefin-based polymer having a high molecular weight and a wide molecular weight distribution may be easily prepared.

The metallocene compound of Chemical Formula 1 may be obtained by connecting the indenoindole derivative and the cyclopentadiene derivative with a bridge compound to prepare a ligand compound, and carrying out metallation by adding a metal precursor compound, but is not limited thereto.

More specifically, for example, after preparing a lithium salt by reacting the indenoindole derivative and the cyclopentadiene derivative with an organic lithium compound such as n-BuLi, a halogenated compound of a bridge compound may be mixed therewith and then this mixture may be reacted to prepare the ligand compound. After mixing the ligand compound or the lithium salt thereof and the metal precursor compound, and reacting them for about 12 to 24 h until the reaction is completed, the reaction mixture may be filtered and dried under reduced pressure to obtain the metallocene compound represented by Chemical Formula 1.

A preparation method of the metallocene compound of the present invention is concretely explained in the following examples.

The present invention also provides a catalyst composition including the metallocene compound and a cocatalyst.

The catalyst composition according to the present invention may further include one or more of cocatalyst compounds represented by the following Chemical Formula 3, Chemical Formula 4, and Chemical Formula 5, in addition to the metallocene compound:

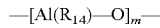  [Chemical Formula 3]

wherein, in Chemical Formula 3, $R_{14}$'s may be the same as or different from each other, and are each independently a halogen; a hydrocarbon having 1 to 20 carbon atoms; or a halogen-substituted hydrocarbon having 1 to 20 carbon atoms; and m is an integer of 2 or more;

  [Chemical Formula 4]

wherein, in Chemical Formula 4, $R_{14}$'s may be the same as defined in Chemical Formula 3; and J is aluminum or boron;

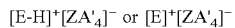  [Chemical Formula 5]

wherein, in Chemical Formula 5,

E is a neutral or cationic Lewis acid;

H is a hydrogen atom;

Z is a Group 13 element; and

A's may be the same as or different from each other, and are each independently an aryl group having 6 to 20 carbon atoms or an alkyl group having 1 to 20 carbon atoms, of which one or more hydrogen atoms are unsubstituted or substituted with a halogen, a hydrocarbon having 1 to 20 carbon atoms, alkoxy, or phenoxy.

Examples of the compound represented by Chemical Formula 3 may include methylaluminoxane, ethylaluminoxane, isobutylaluminoxane, butylaluminoxane, or the like, and a more preferred compound may be methylaluminoxane.

Examples of the compound represented by Chemical Formula 4 may include trimethylaluminum, triethylaluminum, triisobutylaluminum, tripropylaluminum, tributylaluminum, dimethylchloroaluminum, triisopropylaluminum, tri-s-butylaluminum, tricyclopentylaluminum, tripentylaluminum, triisopentylaluminum, trihexylaluminum, trioctylaluminum, ethyldimethylaluminum, methyldiethylaluminum, triphenylaluminum, tri-p-tolylaluminum, dimethylaluminummethoxide, dimethylaluminumethoxide, trimethylboron, triethylboron, triisobutylboron, tripropylboron, tributylboron, or the like, and a more preferred compound may be selected from trimethylaluminum, triethylaluminum, and triisobutylaluminum.

Examples of the compound represented by Chemical Formula 5 may include triethylammonium tetraphenylboron, tributylammonium tetraphenylboron, trimethylammonium tetraphenylboron, tripropylammonium tetraphenylboron, trimethylammonium tetra(p-tolyl)boron, trimethylammonium tetra(o,p-dimethylphenyl)boron, tributylammonium tetra(p-trifluoromethylphenyl)boron, trimethylammonium tetra(p-trifluoromethylphenyl)boron, tributylammonium tetrapentafluorophenylboron, N,N-diethylanilinium tetraphenylboron, N,N-diethylanilinium tetrapentafluorophenylboron, diethylammonium tetrapentafluorophenylboron, triphenylphosphonium tetraphenylboron, trimethylphosphonium tetraphenylboron, triethylammonium tetraphenylaluminum, tributylammonium tetraphenylaluminum, trimethylammonium tetraphenylaluminum, tripropylammonium tetraphenylaluminum, trimethylammonium tetra(p-tolyl)aluminum, tripropylammonium tetra(p-tolyl)aluminum, triethylammonium tetra(o,p-dimethylphenyl)aluminum, tributylammonium tetra(p-trifluoromethylphenyl)aluminum, trimethylammonium tetra(p-trifluoromethylphenyl)aluminum, tributylammonium tetrapentafluorophenylaluminum, N,N-diethylanilinium tetraphenylaluminum, N,N-diethylanilinium tetrapentafluorophenylaluminum, diethylammonium tetrapentatetraphenylaluminum, triphenylphosphonium tetraphenylaluminum, trimethylphosphonium tetraphenylaluminum, tripropylammonium tetra(p-tolyl)boron, triethylammonium tetra(o,p-dimethylphenyl)boron, tributylammonium tetra(p-trifluoromethylphenyl)boron, triphenylcarbonium tetra(p-trifluoromethylphenyl)boron, triphenylcarbonium tetrapentafluorophenylboron, or the like.

Alumoxane may be preferably used, and an alkyl alumoxane, methylalumoxane (MAO), may be more preferably used.

The catalyst composition according to the present invention may be prepared by a first method including the steps of 1) contacting the metallocene compound represented by Chemical Formula 1 with the compound represented by Chemical Formula 3 or Chemical Formula 4 to obtain a mixture; and 2) adding the compound represented by Chemical Formula 5 to the mixture.

Further, the catalyst composition according to the present invention may be prepared by a second method of contacting the metallocene compound represented by Chemical Formula 1 with the compound represented by Chemical Formula 3.

In the first method of preparing the catalyst composition, a molar ratio of the metallocene compound represented by Chemical Formula 1/the compound represented by Chemical Formula 3 or Chemical Formula 4 is preferably 1/5,000 to 1/2, more preferably 1/1,000 to 1/10, and most preferably 1/500 to 1/20. When the molar ratio of the metallocene compound represented by Chemical Formula 1/the compound represented by Chemical Formula 3 or Chemical Formula 4 exceeds 1/2, there is a problem that an alkylating agent amount is very small and the metal compound is not completely alkylated, and when the molar ratio is less than 1/5,000, the alkylation of the metal compound is accomplished, but there is a problem that the alkylated metal compound is not completely activated due to the side reaction between remaining excess alkylating agent and the activator of Chemical Formula 5. Furthermore, the molar ratio of the metallocene compound represented by Chemical Formula 1/the compound represented by Chemical Formula 5 is preferably 1/25 to 1, more preferably 1/10 to 1, and most preferably 1/5 to 1. When the molar ratio of the metallocene compound represented by Chemical Formula 1/the compound represented by Chemical Formula 5 exceeds 1, there is a problem that the activity of the prepared catalyst composition is deteriorated because the activator amount is relatively small and the metal compound is not completely activated, and when the molar ratio is less than 1/25, the activation of the metal compound is completely accomplished, but there is a problem that the cost of the catalyst composition is not economical or the purity of the polymer to be prepared is decreased due to the remaining excess activator.

In the second method of preparing the catalyst composition, the molar ratio of the metallocene compound represented by Chemical Formula 1/the compound represented by Chemical Formula 3 is preferably 1/10,000 to 1/10, more preferably 1/5,000 to 1/100, and most preferably 1/3,000 to 1/500. When the molar ratio exceeds 1/10, there is a problem that the activity of the prepared catalyst composition is deteriorated because the activator amount is relatively small and the metal compound is not completely activated, and when the molar ratio is less than 1/10,000, the activation of the metal compound is completely accomplished, but there is a problem that the cost of the catalyst composition is not economical or the purity of the polymer to be prepared is decreased due to the remaining excess activator.

As a reaction solvent used upon preparation of the catalyst composition, a hydrocarbon solvent such as pentane, hexane, heptane, etc., or an aromatic solvent such as benzene, toluene, etc., may be used.

Furthermore, the catalyst composition may include the metallocene compound and the cocatalyst compound in the form of being supported on a support.

When the metallocene compound and the cocatalyst compound are used in the form of being supported on the support, the metallocene compound may be included in an amount of about 0.5 to about 20 parts by weight and the cocatalyst may be included in an amount of about 1 to about 1,000 parts by weight, based on 100 parts by weight of the support. Preferably, the metallocene compound may be included in an amount of about 1 to about 15 parts by weight and the cocatalyst may be included in an amount of about 10 to about 500 parts by weight, based on 100 parts by weight of the support. Most preferably, the metallocene compound may be included in an amount of about 1 to about 100 parts by weight and the cocatalyst may be included in an amount of about 40 to about 150 parts by weight, based on 100 parts by weight of the support.

Meanwhile, as long as the support is a metal, a metal salt, or a metal oxide which is commonly used in a supported catalyst, there is no limitation in the constitution. Specifically, the support may include any one support selected from the group consisting of silica, silica-alumina, and silica-magnesia. The support may be dried at a high temperature, and generally it may include an oxide, a carbonate, a sulfate, or a nitrate of a metal, such as $Na_2O$, $K_2CO_3$, $BaSO_4$, $Mg(NO_3)_2$, etc.

It is better that the amount of hydroxy (—OH) groups on the surface of the support is as small as possible, but it is practically difficult to eliminate all of hydroxy groups. The amount of hydroxy groups may be controlled by the preparation method, the preparation conditions, and the drying conditions (temperature, time, drying method, etc.) of the support, and the amount of hydroxy groups is preferably 0.1 mmol/g to 10 mmol/g, more preferably 0.1 mmol/g to 1 mmol/g, and more preferably 0.1 mmol/g to 0.5 mmol/g. In order to reduce the side-reaction by some hydroxy groups left after drying, a support, from which hydroxy groups are chemically eliminated while preserving highly reactive siloxane groups participating in supporting, may be used.

Further, the present invention provides a method of preparing an olefin-based polymer, including the step of polymerizing olefin-based monomers in the presence of the catalyst composition including the metallocene compound, and an olefin-based polymer prepared by the preparation method.

The polymerization reaction may be carried out according to a solution polymerization process, a slurry process, or a gas phase process by using a continuous slurry polymerization reactor, a loop slurry reactor, a gas phase reactor, or a solution reactor. Furthermore, the reaction may be homopolymerization of an olefin-based monomer or copolymerization of two or more monomers.

The polymerization of the olefin-based monomer may be carried out at a temperature of about 25° C. to about 500° C. and at a pressure of about 1 kgf/cm² to about 100 kgf/cm² for about 1 h to about 24 h. Specifically, the polymerization of the olefin-based monomer may be carried out at a temperature of about 25° C. to about 500° C., preferably about 25° C. to about 200° C., and more preferably, about 50° C. to about 100° C. Furthermore, the reaction pressure may be about 1 kgf/cm² to about 100 kgf/cm², preferably about 1 kgf/cm² to about 50 kgf/cm², and more preferably about 5 kgf/cm² to about 40 kgf/cm².

In the olefin-based polymer prepared according to the present invention, specific examples of the olefin-based monomer may include ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-eicosene, or the like, and the olefin-based monomer may be a copolymer prepared by copolymerizing two or more of the monomers.

The olefin-based polymer may be a polyethylene polymer, but is not limited thereto.

If the olefin-based polymer is a copolymer of ethylene/alpha-olefin, the content of a comonomer, alpha-olefin, is not particularly limited, and it may be adequately selected according to the use or purpose of the olefin-based polymer. More specifically, the content may be more than 0 mol % and 99 mol % or less.

The olefin-based polymer prepared by the method may exhibit a high molecular weight and good copolymerization ability.

According to an embodiment of the present invention, a weight average molecular weight (Mw) of the olefin-based polymer may be about 50,000 g/mol to about 3,000,000 g/mol, or about 50,000 g/mol to about 2,000,000 g/mol, or about 50,000 g/mol to about 500,000 g/mol.

Furthermore, a molecular weight distribution (Mw/Mn) of the olefin-based polymer may be about 3 to about 20, about 3 to about 15, about 3 to about 12, or about 5 to about 12.

In addition, according to an embodiment of the present invention, the density of the olefin-based polymer may be about 0.85 g/cm³ to about 0.96 g/cm³, and preferably about 0.90 g/cm³ to about 0.95 g/cm³.

Therefore, the olefin-based polymer according to the present invention shows a high molecular weight, thereby being applied to a variety of fields according to its use.

Hereinafter, preferred examples are provided for better understanding. However, these examples are for illustrative purposes only, and the invention is not intended to be limited by these examples.

EXAMPLES

Preparation Example of Metallocene Compound

Preparation Example 1

1-1. Synthesis of Ligand Compound

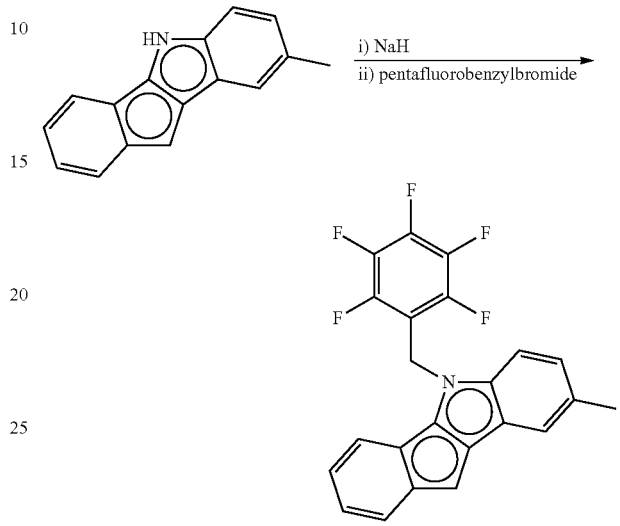

4.5 g (20 mmol) of 8-methyl-5,10-dihydroindeno[1,2-b]indole in a DMF solution was used in the reaction. A 100 mL Schlenk flask was prepared and placed in a glove box, 0.58 g (24 mmol) of NaH was weighed in the glove box, and then taken out of the glove box. NaH was dissolved in 50 mL of DMF, and then added dropwise to an indenoindole solution via a cannula in a dry ice/acetone bath. After complete addition, the temperature of the mixture was slowly raised to room temperature, followed by agitation overnight. After sampling, this reaction mixture was reacted with D₂O, and then 75% deprotonation of the amine proton of indenoindole was confirmed by ¹H NMR.

10 g of 4 Åmolecular sieves was placed in another 100 mL Schlenk flask. At 1 h after reducing the pressure under vacuum, 50 mL of DMF and 2.9 mL (20 mmol) of 2,3,4,5,6-pentafluorobenzyl bromide were injected under an Ar condition. At 30 min after injection, the solution was added dropwise to an indenoindole solution via a cannula in a dry ice/acetone bath, followed by agitation at room temperature overnight. After reaction, extraction was performed with ether/water, and residual water was removed from an organic layer with MgSO₄ and the solvent was removed under reduced pressure to obtain a reaction mixture in an oil phase. Before separation of materials, the reaction mixture was identified by ¹H NMR, and as a result, N and C alkylation was found to be 66:34.

About 30 mL of MeOH was added to the reaction mixture, and an ivory colored solid was obtained by filtration. TLC (etherhexane=1:4) showed that most of reaction by-products were dissolved in the filtrate, but J304U was also found in the filtrate. Therefore, additional washing of a filter cake with MeOH was not performed. The MeOH filter cake was washed with about 50 mL of hexane, and then washed with 15 mL of ether twice to separate 0.26 g (0.65 mmol) of 8-methyl-5-((perfluorophenyl)methyl)-5,10-dihydroindeno[1,2-b]indole as a white solid product.

¹H NMR (500 MHz, CDCl3): 7.66-6.95 (7H, m), 5.70 (2H, s), 3.68 (2H, s), 2.43 (3H, s).

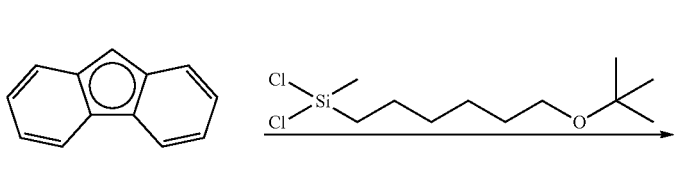 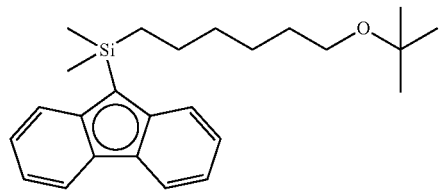

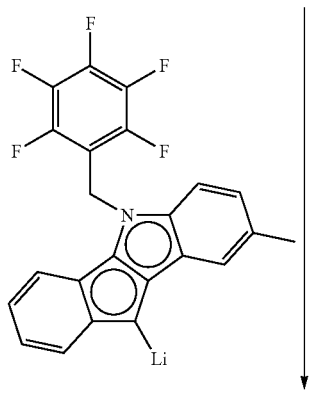

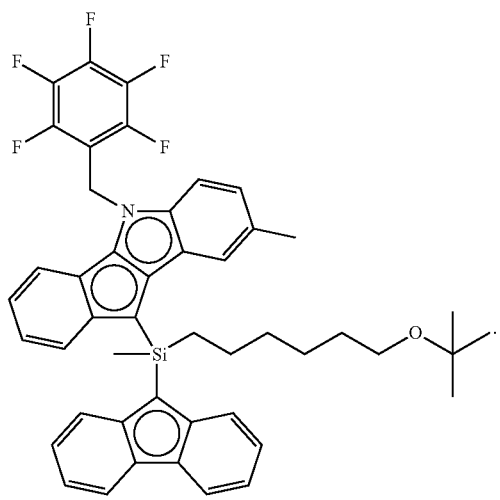

0.83 g (5 mmol) of fluorene was added to a dry 250 mL Schlenk flask, and 50 mL of hexane and 3 mL of ether were injected therein. This solution was cooled to −78° C., and then the air in the flask was replaced by argon. 2.4 mL (6 mmol) of a 2.5 M nBuLi hexane solution was slowly added dropwise, and then the temperature of the reaction mixture was slowly raised to room temperature, followed by agitation until the next day. Another 250 mL Schlenk flask was prepared and placed in a glove box. 1.36 g (5 mmol) of (6-tert-butoxyhexyl)dichloro(methyl)silane was weighed in the glove box, and then taken out of the glove box, and 80 mL of hexane was injected thereto, followed by agitation. This flask was cooled to −78° C., and then a lithiated solution of fluorene was very slowly added dropwise thereto via a cannula. After completion of injection, the temperature of the mixture was raised to room temperature, and then allowed to react overnight. After reaction overnight, the solvent was removed, and in the glove box, the reaction was confirmed by NMR.

$^1$H NMR (500 MHz, $C_5D_5$): −0.01 (3H, s), 1.12 (9H, m), 1.03-1.46 (10H, m), 3.17 (2H, t), 3.87 (1H, s), 7.15-7.78 (8H, m)

After confirming synthesis of a silicon-tethered fluorene part, 1.99 g (5 mmol) of the synthesized 8-methyl-5-((perfluorophenyl)methyl)-5,10-dihydroindeno[1,2-b]indole was injected to a dry 250 mL Schlenk flask, and dissolved in 100 mL of THF. Thereafter, 2.4 mL (6 mmol) of a 2.5 M nBuLi hexane solution was slowly added dropwise at −78° C., followed by agitation for a day. The lithiated solution of silicon-tethered fluorene synthesized previously was slowly added dropwise at −78° C. After reaction overnight, 50 mL of water was injected into the flask for quenching. An organic layer was separated and dried with MgSO$_4$. From the mixture obtained by filtration, all the solvents were removed under reduced pressure to give an oily product.

$^1$H NMR (500 MHz, CDCl$_3$): −0.11 (3H, s), 1.13 (9H, m), 0.86-1.49 (10H, m), 2.64 (3H, s), 3.26 (2H, m), 3.67 (1H, s), 4.98 (1H, s), 5.69 (2H, s), 7.20-7.85 (15H, m)

1-2. Synthesis of Metallocene Compound 4.1 g (5.3 mmol) of the ligand synthesized in 1-1 was added to a dry 250 mL Schlenk flask, and dissolved in 50 mL of toluene. Then, 2 mL of ether was added thereto, and 5 mL (12.5 mmol) of a 2.5 M nBuLi hexane solution was added for lithiation. After one day, 1.96 g (5.2 mmol) of ZrCl$_4$(THF)$_2$ was added into a 250 mL Schlenk flask and toluene was added to prepare a suspension, in a glove box. Both of the flasks were cooled to −78° C., and the lithiated ligand was slowly added to the Zr suspension. After injection, the temperature of the reaction mixture was slowly raised to room temperature, and then allowed to react for one day. Then, this mixture was filtered in a filter system without contact with air to remove LiCl. After removal of all the solvents, recrystallization was performed with hexane, and then filtration was further performed to obtain a product in a yield of 55.2%.

$^1$H NMR (500 MHz, CDCl$_3$): 1.12 (9H, m), 1.62 (3H, s), 0.85-2.65 (10H, m), 2.33 (3H, s), 3.36 (2H, m), 5.60 (2H, s), 6.98-7.83 (15H, m)

Preparation Example 2

2-1. Synthesis of Ligand Compound

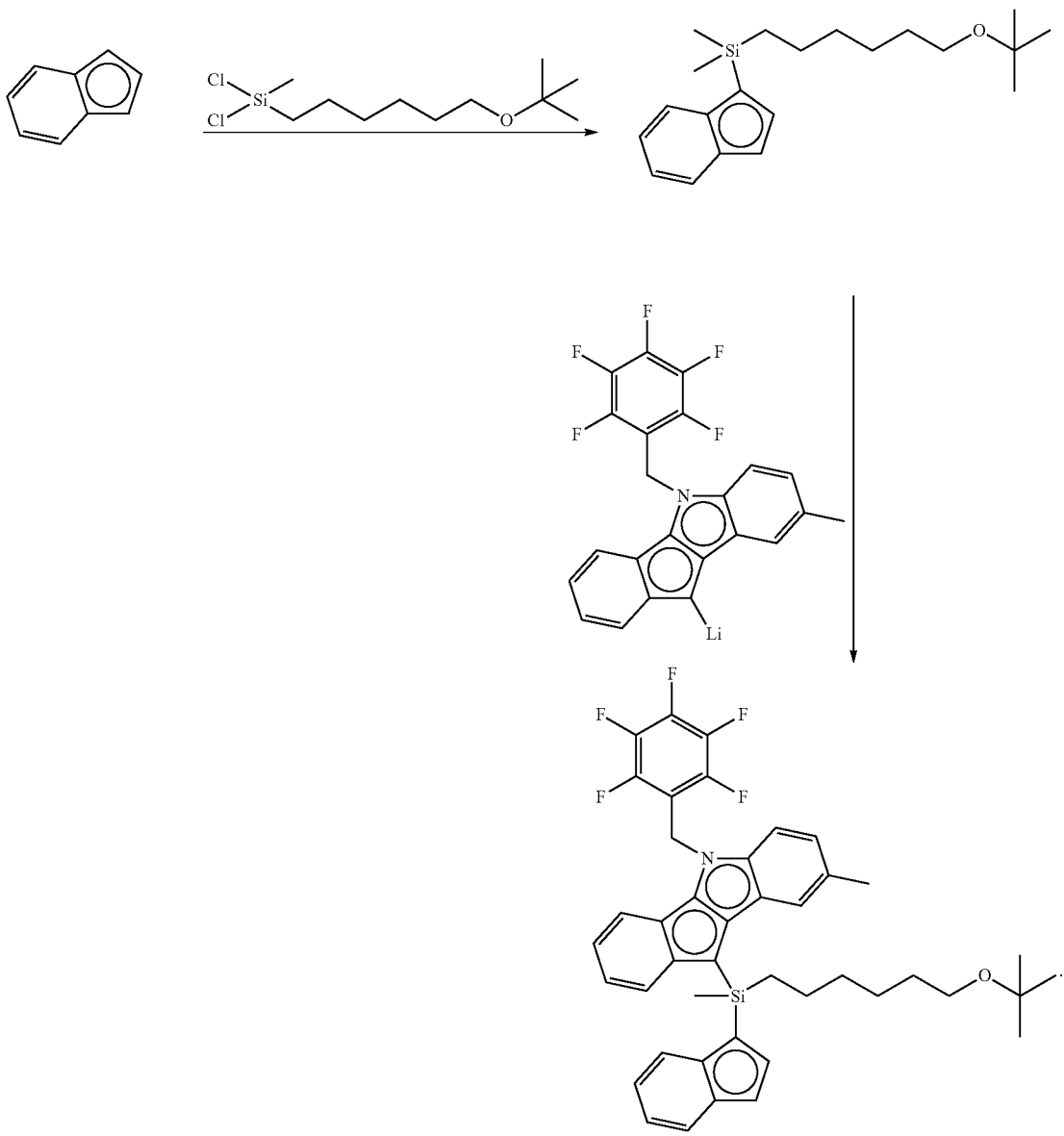

0.65 g (5 mmol) of indene was added to a dry 250 mL Schlenk flask, and 50 mL of hexane and 3 mL of ether were injected therein. This solution was cooled to −78° C., and then the air in the flask was replaced by argon. 2.4 mL (6 mmol) of a 2.5 M nBuLi hexane solution was slowly added dropwise, and then the temperature of the reaction mixture was slowly raised to room temperature, followed by agitation until the next day. Another 250 mL Schlenk flask was prepared and placed in a glove box. 1.36 g (5 mmol) of (6-tert-butoxyhexyl)dichloro(methyl)silane was weighed in the glove box, and then taken out of the glove box, and 80 mL of hexane was injected thereto, followed by agitation. This flask was cooled to −78° C., and then a lithiated solution of indene was very slowly added dropwise thereto via a cannula. After completion of injection, the temperature of the mixture was raised to room temperature, and then allowed to react overnight. After reaction overnight, the solvent was removed, and in the glove box, the reaction was confirmed by NMR.

$^1$H NMR (500 MHz, CDCl3): 0.23 (3H, d), 1.37 (9H, s), 0.81-1.56 (10H, m), 3.38 (2H, m) 3.88 (1H, s), 6.77 (1H, dd), 7.11 (1H, d), 7.28-7.72 (4H, m)

After confirming synthesis of a silicon-tethered indene part, it was dissolved in THF, and 2 g (5 mmol) of 8-methyl-5-((perfluorophenyl)methyl)-5,10-dihydroindeno[1,2-b]indole was injected to a dry 250 mL Schlenk flask, and dissolved in 50 mL of THF. Thereafter, 2.4 mL (6 mmol) of a 2.5 M nBuLi hexane solution was slowly added dropwise at −78° C., followed by agitation for a day. The lithiated solution of 8-methyl-5-((perfluorophenyl)methyl)-5,10-dihydroindeno[1,2-b]indole was slowly added dropwise to the silicon-tethered indene part synthesized previously at −78° C. After reaction overnight, 50 mL of water was injected into the flask for quenching. An organic layer was separated and dried with MgSO4. From the mixture obtained by filtration, all the solvents were removed under reduced pressure to give an oily product.

$^1$H NMR (500 MHz, CDCl3): −0.21 (3H, m), 1.15 (9H, m), 0.87-1.48 (10H, m), 2.34 (3H, d), 2.43 (1H, d), 3.28 (2H, m), 3.66 (1H, d), 5.69 (2H, s), 6.01 (1H, d), 6.34 (1H, d), 6.97-7.70 (11H, m)

2-2. Synthesis of Metallocene Compound 4.03 g (5.6 mmol) of the ligand synthesized in 2-1 was added to a dry 250 mL Schlenk flask, and dissolved in 50 mL of toluene. Then, 2 mL of ether was added thereto and 5.2 mL (12.8 mmol) of a 2.5 M nBuLi hexane solution was added for lithiation. After one day, 2.03 g (5.4 mmol) of ZrCl4(THF)2 was added into a 250 mL schlenk flask, and toluene was added to prepare a suspension, in a glove box. Both of the two flasks were cooled to −78° C., and the lithiated ligand was slowly added to the Zr suspension. After injection, the temperature of the reaction mixture was slowly raised to room temperature, and then allowed to react for one day. Then, this mixture was filtered in a filter system without contact with air to remove LiCl. After removal of all the solvents, recrystallization was performed with hexane, and then filtration was further performed to obtain a product in a yield of 52.2%.

$^1$H NMR (500 MHz, CDCl3): 1.18 (9H, m), 1.38 (3H, s), 0.81-1.86 (10H, m), 2.43 (H, s), 3.27 (2H, m), 5.70 (2H, s), 6.11 (2H, m), 6.98-7.59 (11H, m)

Preparation Example 3

3-1. Synthesis of Ligand Compound

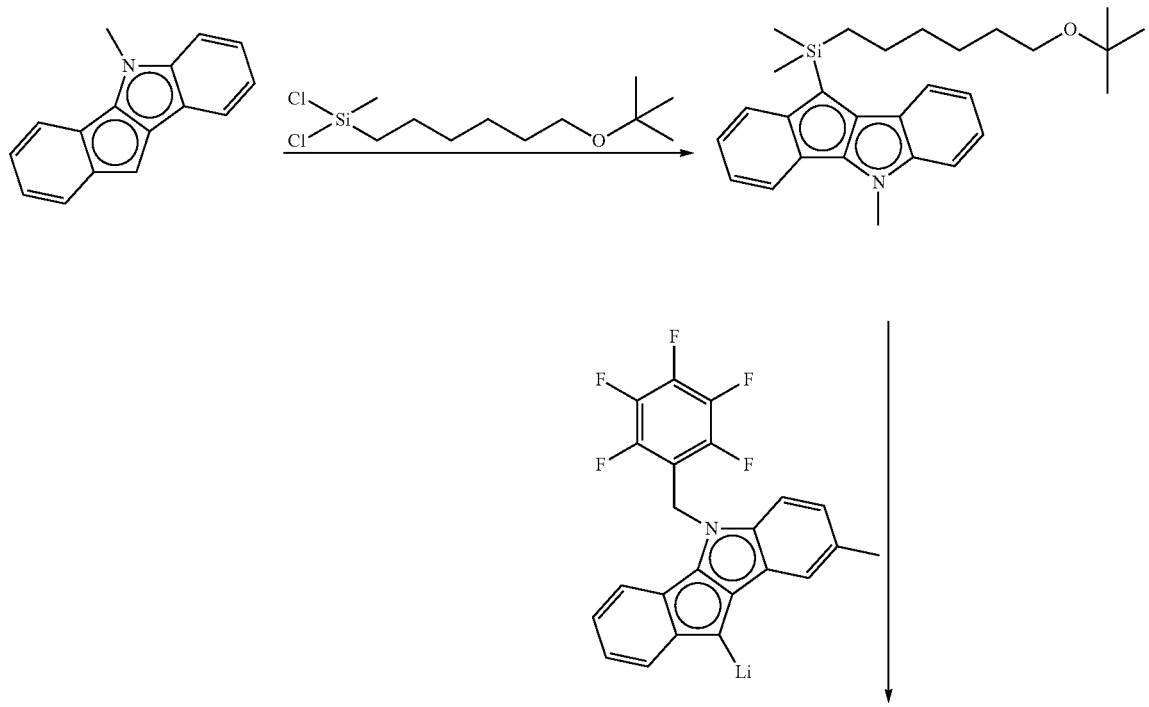

-continued

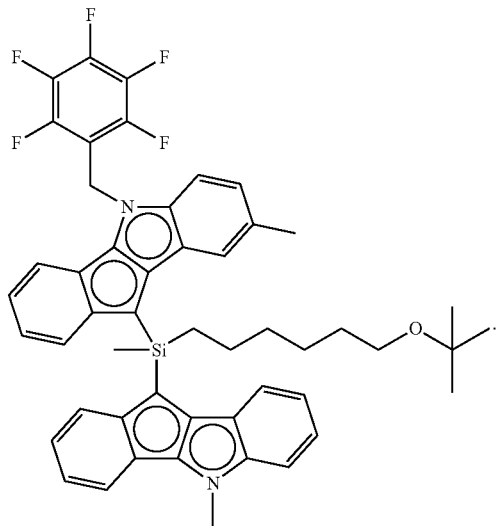

1.1 g (5 mmol) of 5-methyl-5,10-dihydroindeno[1,2-b]indole was added to a dry 250 mL Schlenk flask, and 80 mL of hexane and 3 mL of ether were injected therein. This solution was cooled to −78° C., and then the air in the flask was replaced by argon. 2.4 mL (6 mmol) of a 2.5 M nBuLi hexane solution was slowly added dropwise, and then the temperature of the reaction mixture was slowly raised to room temperature, followed by agitation until the next day. Another 250 mL Schlenk flask was prepared and placed in a glove box. 1.36 g (5 mmol) of (6-tert-butoxyhexyl)dichloro(methyl)silane was weighed in the glove box, then taken out of the glove box, and 80 mL of hexane was injected thereto, followed by agitation. This flask was cooled to −78° C., and then a lithiated solution of 5-methyl-5,10-dihydroindeno[1,2-b]indole was very slowly added dropwise thereto via a cannula. After completion of injection, the temperature of the mixture was slowly raised to room temperature, and then allowed to react overnight. After reaction overnight, the solvent was removed, and in the glove box, the reaction was confirmed by NMR.

$^1$H NMR (500 MHz, CDCl3): 0.301 (3H, d), 1.15 (9H, m), 0.87-1.49 (10H, m), 3.28 (2H, m) 3.70 (1H, s), 4.05 (3H, d), 7.13-7.74 (8H, m)

After confirming synthesis of a silicon-tethered 5-methyl-5,10-dihydroindeno[1,2-b]indole part, 2 g (5 mmol) of 8-methyl-5-((perfluorophenyl)methyl)-5,10-dihydroindeno[1,2-b]indole was injected to a dry 250 mL Schlenk flask, and dissolved in 50 mL of THF. Thereafter, 2.4 mL (6 mmol) of a 2.5 M nBuLi hexane solution was slowly added dropwise at −78° C., followed by agitation for a day. The silicon-tethered 5-methyl-5,10-dihydroindeno[1,2-b]indole part synthesized previously was dissolved in 50 ml of THF, and then the lithiated solution of 8-methyl-5-((perfluorophenyl)methyl)-5,10-dihydroindeno[1,2-b]indole was slowly added dropwise at −78° C. After reaction overnight, 50 mL of water was injected to the flask for quenching. An organic layer was separated and dried with MgSO$_4$. From the mixture obtained by filtration, all the solvents were removed under reduced pressure to give an oily product.

$^1$H NMR (500 MHz, CDCl3): 0.00 (3H, s), 1.17 (9H, m), 0.87-1.51 (10H, m), 2.43 (3H, d), 3.27 (2H, m), 3.67 (1H, d), 3.88 (1H, d), 4.09 (3H, d), 5.68 (2H, d), 6.96-7.74 (15H, m)

3-2. Synthesis of Metallocene Compound 4.3 g (5.2 mmol) of the ligand synthesized in 3-1 was added to a dry 250 mL Schlenk flask, and dissolved in 80 mL of toluene. Then, 3 mL of ether was added thereto, and 4.85 mL (12 mmol) of 2.5 M nBuLi hexane solution was added for lithiation. After one day, 1.9 g (5.1 mmol) of ZrCl$_4$(THF)$_2$ was added into a 250 mL Schlenk flask and toluene was added to prepare a suspension, in a glove box. Both of the two flasks were cooled to −78° C., and the lithiated ligand was slowly added to the Zr suspension. After injection, the temperature of the reaction mixture was slowly raised to room temperature, and then allowed to react for one day. Then, this mixture was filtered in a filter system without contact with air to remove LiCl. After removal of all the solvents, recrystallization was performed with hexane, and then filtration was further performed to obtain a product in a yield of 54%.

$^1$H NMR (500 MHz, CDCl3): 1.16 (9H, m), 1.81 (3H, s), 1.40-2.65 (10H, m), 3.28 (2H, m), 3.70 (3H, s), 4.08 (3H, s), 5.70 (2H, s), 6.46-7.65 (15H, m)

Preparation Examples of Supported Catalysts

Preparation Example 4

A silica support was prepared by dehydrating silica (SYLOPOL 948, produced by Grace Davison Co.) at 400° C. under vacuum for 12 h.

After adding 100 mL of a toluene solution in a glass reactor at room temperature and adding 10 g of the prepared silica support, the solution was agitated while elevating the temperature of the reactor to 40° C. When the silica was sufficiently dispersed, 60.6 mL of a 10 wt % methylaluminoxane (MAO)/toluene solution was added thereto and the mixture was agitated at 200 rpm for 16 h after elevating the temperature to 80° C. Subsequently, the temperature was decreased to 40° C., and the unreacted aluminum compound was eliminated by washing with a sufficient amount of toluene. After adding 100 mL of toluene therein, 0.5 mmol of the metallocene compound prepared in Preparation Example 1 was added thereto and the mixture was agitated for 2 h. After stopping agitation when the reaction was completed, a toluene layer was separated and eliminated therefrom, and the supported catalyst was obtained by reducing the pressure at 40° C. to eliminate the remaining toluene.

Preparation Example 5

A supported catalyst was prepared in the same manner as in Preparation Example 4, except that 0.5 mmol of the metallocene compound prepared in Preparation Example 2 was used.

Comparative Preparation Example 1

A supported catalyst was prepared in the same manner as in Preparation Example 4, except that 0.5 mmol of (tert-Bu—O—$(CH_2)_6$)MeSi(9-$C_{13}H_9$)$_2$ZrCl$_2$ prepared according to Preparation Example 1 of Korean Patent No. 1154507 was used.

Examples of Solution Polymerization

Polymerization of Ethylene

Example 1

A 300 mL Andrew bottle was prepared and assembled with an impeller part, and then air in the bottle was replaced by argon in a glove box. After adding 235 mL of toluene to the Andrew bottle, 10 mL of an MAO (10 wt % in toluene) solution was added thereto. 20 μmol of the metallocene compound catalyst prepared in Preparation Example 1 was added to a separate 100 mL flask and dissolved in 20 mL of toluene. 5 mL (5 μmol) of the catalyst solution was taken and injected to the Andrew bottle, followed by agitation for 5 min. The Andrew bottle was immersed in an oil bath heated to 90° C. and the mixture was agitated for 5 min by using a mechanical stirrer fixed at the upper part of the bottle until the temperature of the reaction solution reached 90° C. The air in the bottle was purged with ethylene gas 3 times, and pressure was slowly raised up to 50 psig by opening an ethylene valve. The reaction was allowed to continue for 15 min while operating the mechanical stirrer at 500 rpm while maintaining the pressure by continuously providing ethylene of as much as was consumed. When the reaction was completed, the gas in the reactor was slowly vented after locking the ethylene valve and stopping agitation. After disassembling the cover of the reactor, the reactant was poured in 400 mL of an ethanol/HCl aqueous solution mixture, and the mixture was agitated for about 2 h. The polymer obtained by filtration was dried at 65° C. for 20 h in a vacuum oven. The obtained polymer was weighed to calculate the activity of the catalyst, and used for additional analysis.

Examples 2 and 3

Ethylene polymerization was carried out in the same manner as in Example 1, except that the metallocene compound catalysts of Preparation Examples 2 and 3 were used, respectively, and polymers thus obtained were analyzed.

Copolymerization of Ethylene-1-Hexene

Example 4

A 300 mL Andrew bottle was prepared and assembled with an impeller part, and then air in the bottle was replaced by argon in a glove box. After adding 235 mL of toluene to the Andrew bottle, 10 mL of an MAO (10 wt % in toluene) solution was added thereto. 20 μmol of the metallocene compound catalyst prepared in Preparation Example 1 was added to a separate 100 mL flask and dissolved in 20 mL of toluene. 5 mL (5 μmol) of the catalyst solution was taken and injected into the Andrew bottle, followed by agitation for 5 min. The Andrew bottle was immersed in an oil bath heated to 90° C. and the mixture was agitated for 5 min by using a mechanical stirrer fixed at the upper part of the bottle until the temperature of the reaction solution reached 90° C. After stopping the agitation, 5 mL of 1-hexene was injected under an argon atmosphere, the air in the bottle was purged with ethylene gas 3 times, and pressure was slowly raised up to 50 psig by opening an ethylene valve. The reaction was allowed to continue for 15 min while operating the mechanical stirrer at 500 rpm while maintaining the pressure by continuously providing ethylene of as much as was consumed. When the reaction was completed, the gas in the reactor was slowly vented after locking the ethylene valve and stopping agitation. After disassembling the cover of the reactor, the reactant was poured in 400 mL of an ethanol/HCl aqueous solution mixture, and the mixture was agitated for about 2 h. The polymer obtained by filtration was dried at 65° C. for 20 h in a vacuum oven. The obtained polymer was weighed to calculate the activity of the catalyst, and used for additional analysis.

Examples 5 and 6

Ethylene-1-hexene copolymerization was carried out in the same manner as in Example 4, except that the metallocene compound catalysts of Preparation Examples 2 to 13 were used, respectively, and the obtained polymers were analyzed.

The activities of the catalysts and the physical properties of the obtained polymers in Examples 1 to 6 are given in the following Table 1.

TABLE 1

| | Catalyst used | 1-Hx input (unit: mL) | Activity (unit: kg/mmol/h) | 1-Hexene content (unit: mol %) | Mw (unit: g/mol) | Mw/Mn |
|---|---|---|---|---|---|---|
| Example 1 | Preparation Example 1 | 0 | 8.6 | — | 331,000 | 5.7 |
| Example 2 | Preparation Example 2 | 0 | 5.4 | — | 150,000 | 11.6 |
| Example 3 | Preparation Example 3 | 0 | 4.0 | — | 50,100 | 3.7 |
| Example 4 | Preparation Example 1 | 5 | 5.0 | 4.6 | 210,000 | 5.2 |

TABLE 1-continued

| | Catalyst used | 1-Hx input (unit: mL) | Activity (unit: kg/mmol/h) | 1-Hexene content (unit: mol %) | Mw (unit: g/mol) | Mw/Mn |
|---|---|---|---|---|---|---|
| Example 5 | Preparation Example 2 | 5 | 13.9 | 6.6 | 67,700 | 5.6 |
| Example 6 | Preparation Example 3 | 5 | 2.9 | 4.5 | 58,600 | 7.6 |

Referring to Table 1, when the metallocene compounds of the present invention were used as catalysts to perform ethylene polymerization and ethylene-1-hexene copolymerization by the solution polymerization method, respectively, a high molecular weight and a wide molecular weight distribution were obtained. Specifically, in the ethylene-1-hexene copolymerization, high copolymerization ability for the comonomer 1-hexene was observed.

Examples of Polymerization by Supported Catalyst

Example 7

A catalyst was prepared by quantifying 30 mg of the supported catalyst prepared in Preparation Example 4 in a dry box, putting it in a 50 mL glass bottle, sealing the bottle with a rubber diaphragm, and taking the bottle out of the dry box. Polymerization was carried out in a temperature-controllable 2-L metal alloy reactor which was equipped with a mechanical stirrer and used at a high pressure.

After putting 1.2 L of hexane, in which 1.0 mmol of triethylaluminum was included, in the reactor and adding the supported catalyst prepared as above to the reactor without contact with air, polymerization was carried out for 1 h with continuously providing an ethylene monomer gas at 80° C. with a pressure of 40 bar. The polymerization was terminated by stopping agitation, and then venting and eliminating the ethylene gas. The polymerization solvent was eliminated from the obtained polymer by filtration, and the polymer was dried at 80° C. for 12 h in a vacuum oven.

Example 8

Polymerization was carried out in the same manner as in Example 7, except that the supported catalyst prepared in Preparation Example 5 was used.

Comparative Example 1

Polymerization was carried out in the same manner as in Example 7, except that the supported catalyst prepared in Comparative Preparation Example 1 was used.

The activities of the catalysts and the molecular weights and distributions of the obtained polymers in Examples 7 to 8 and Comparative Example 1 are given in the following Table 2.

TABLE 2

| | Catalyst used | Activity (unit: kgPE/gCat/h) | Mw (unit: g/mol) | Mw/Mn |
|---|---|---|---|---|
| Example 7 | Preparation Example 4 | 6.6 | 481,000 | 3.1 |
| Example 8 | Preparation Example 5 | 3.1 | 250,000 | 6.2 |
| Comparative Example 1 | Comparative Preparation Example 1 | 5.9 | 377,265 | 2.1 |

Referring to Table 2, when the metallocene compounds of the present invention were supported and used as catalysts to perform supported catalyst polymerization, a high molecular weight and a wide molecular weight distribution were obtained. Specifically, the supported catalysts showed the effect of broadening the molecular weight distribution, compared to the known metallocene compound in Comparative Example 1, indicating that the supported catalysts are advantageous in the preparation of a polymer having a high molecular weight and a wide molecular weight distribution.

The invention claimed is:

1. A metallocene compound represented by the following Chemical Formula 1:

[Chemical Formula 1]

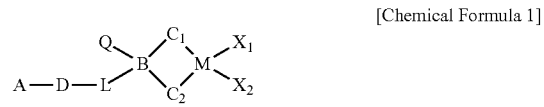

wherein A is hydrogen, a halogen, a C1 to C20 alkyl group, a C2 to C20 alkenyl group, a C6 to C20 aryl group, a C7 to C20 alkylaryl group, a C7 to C20 arylalkyl group, a C1 to C20 alkoxy group, a C2 to C20 alkoxyalkyl group, a C3 to C20 heterocycloalkyl group, or a C5 to C20 heteroaryl group;

D is —O—, —S—, —N(R)—, or —Si(R)(R')—, wherein R and R' are the same as or different from each other, and are each independently hydrogen, a halogen, a C1 to C20 alkyl group, a C2 to C20 alkenyl group, or a C6 to C20 aryl group;

L is a C1 to C10 linear or branched alkylene group;

B is carbon, silicon, or germanium;

Q is hydrogen, a halogen, a C1 to C20 alkyl group, a C2 to C20 alkenyl group, a C6 to C20 aryl group, a C7 to C20 alkylaryl group, or a C7 to C20 arylalkyl group;

M is a Group 4 transition metal;

$X_1$ and $X_2$ are the same as or different from each other, and are each independently a halogen, a C1 to C20 alkyl group, a C2 to C20 alkenyl group, a C6 to C20 aryl group, a nitro group, an amido group, a C1 to C20 alkylsilyl group, a C1 to C20 alkoxy group, or a C1 to C20 sulfonate group; and $C_1$ and $C_2$ are the same as or different from each other, at least one of $C_1$ and $C_2$ is represented by the following Chemical Formula 2, and the other is cyclopentadienyl, indenyl, 4,5,6,7-tetrahydro-1-indenyl, fluorenyl, or indenoindolyl, and they are substituted with a C1 to C20 alkyl group, a C3 to C20 cycloalkyl group, a C6 to C20 aryl group, a C7 to C20 alkylaryl group, or a C7 to C20 arylalkyl group,

[Chemical Formula 2]

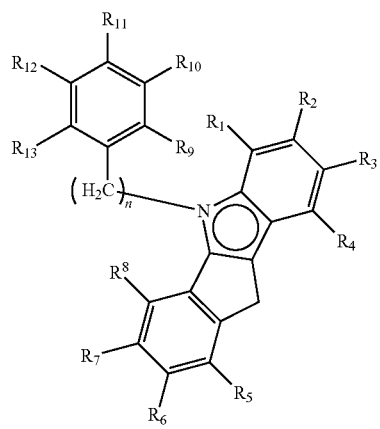

wherein n is an integer of 0 to 5; and $R_1$ to $R_{13}$ are the same as or different from each other, and are each independently hydrogen, a halogen, a C1 to C20 alkyl group, a C2 to C20 alkenyl group, a C1 to C20 alkylsilyl group, a C1 to C20 silylalkyl group, a C1 to C20 alkoxysilyl group, a C1 to C20 alkoxy group, a C6 to C20 aryl group, a C7 to C20 alkylaryl group, or a C7 to C20 arylalkyl group, and at least one of $R_9$ to $R_{13}$ is a halogen.

2. The metallocene compound of claim 1, wherein $R_1$ to $R_{13}$ in Chemical Formula 2 are each independently hydrogen, a halogen, a methyl group, an ethyl group, a propyl group, an isopropyl group, an n-butyl group, a tert-butyl group, a pentyl group, a hexyl group, a heptyl group, an octyl group, a phenyl group, a halogen group, a trimethylsilyl group, a triethylsilyl group, a tripropylsilyl group, a tributylsilyl group, a triisopropylsilyl group, a trimethylsilylmethyl group, a methoxy group, or an ethoxy group.

3. The metallocene compound of claim 1, wherein at least one of $R_9$ to $R_{13}$ in Chemical Formula 2 is fluorine (F).

4. The metallocene compound of claim 1, wherein L in Chemical Formula 1 is a C4 to C8 linear or branched alkylene group.

5. The metallocene compound of claim 1, wherein A in Chemical Formula 1 is hydrogen, a methyl group, an ethyl group, a propyl group, an isopropyl group, an n-butyl group, a tert-butyl group, a methoxymethyl group, a tert-butoxymethyl group, a 1-ethoxyethyl group, a 1-methyl-1-methoxyethyl group, a tetrahydropyranyl group, or a tetrahydrofuranyl group.

6. The metallocene compound of claim 1, wherein the compound represented by Chemical Formula 2 is any one of the following structural formulae:

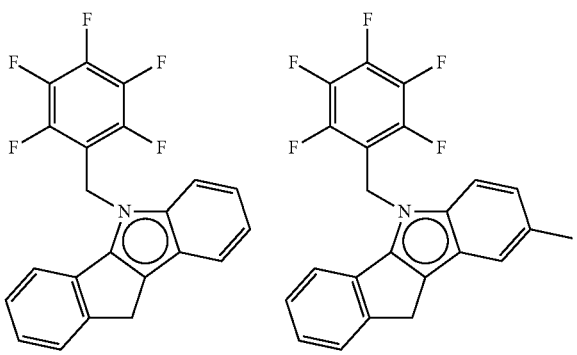

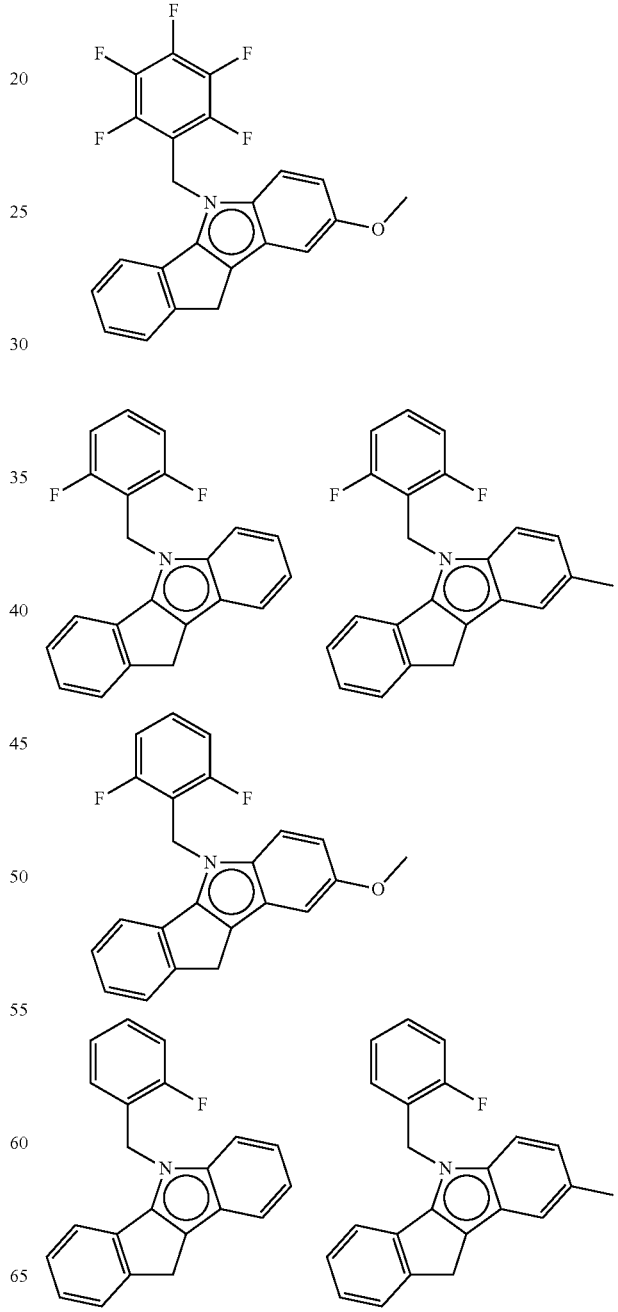

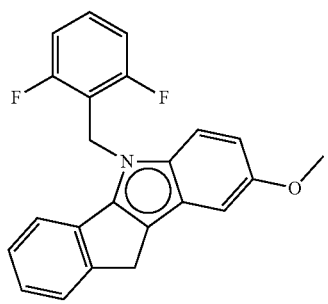
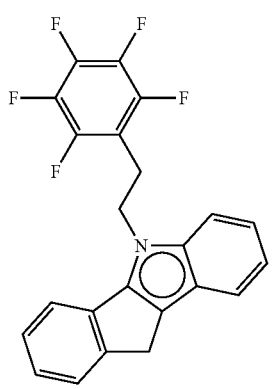
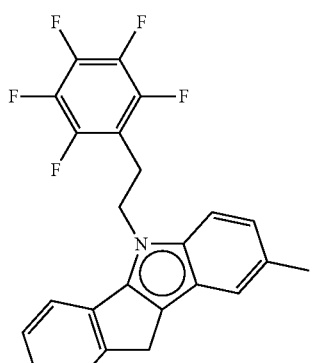
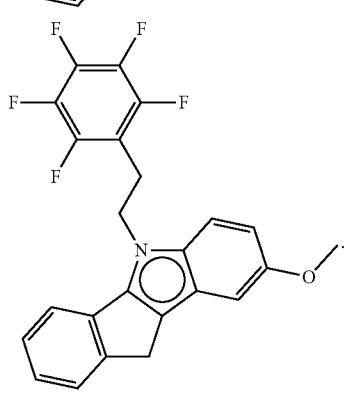
7. The metallocene compound of claim 1, wherein the compound represented by Chemical Formula 1 is any one of the following structural formulae:
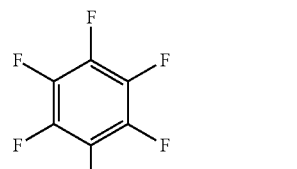
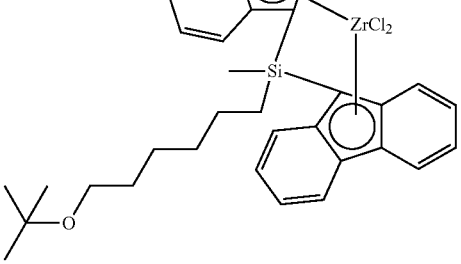
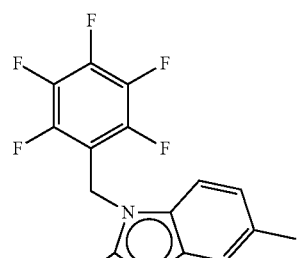
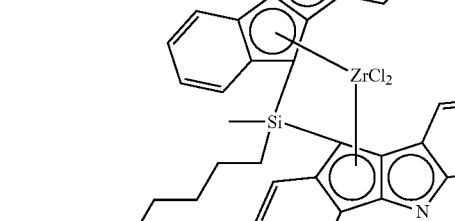

37
-continued
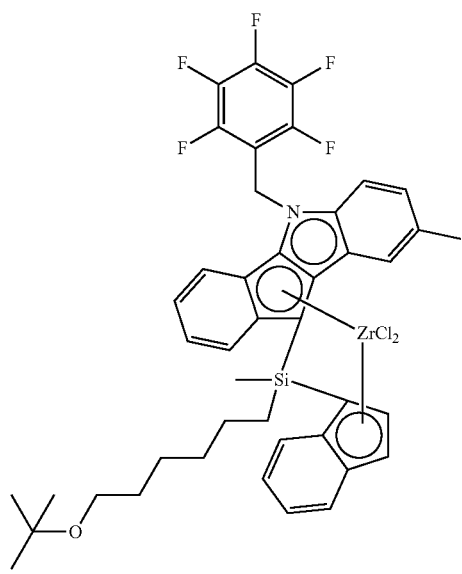
38
-continued
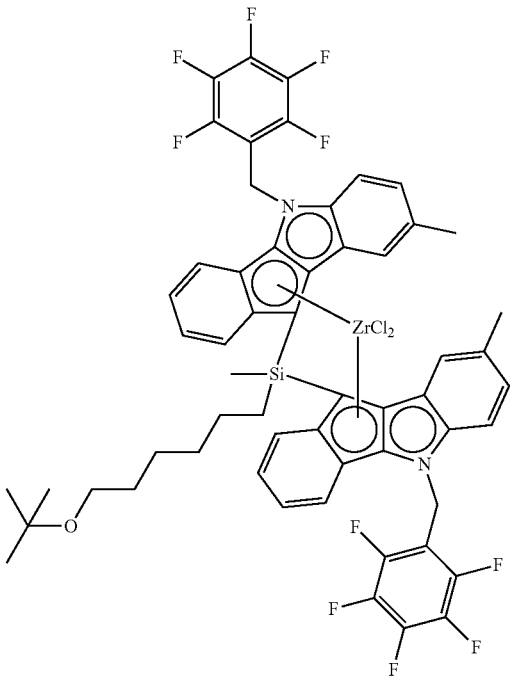
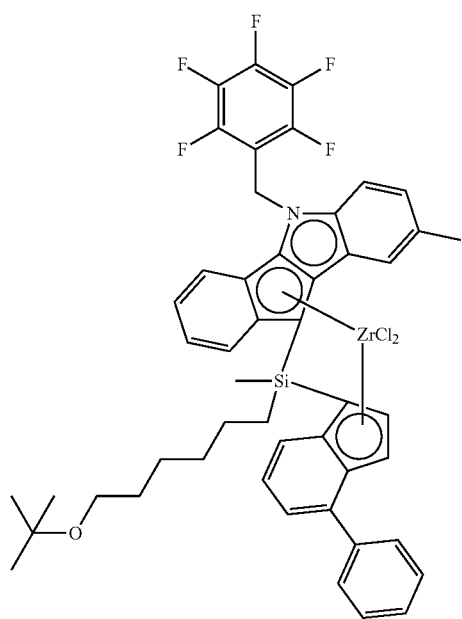
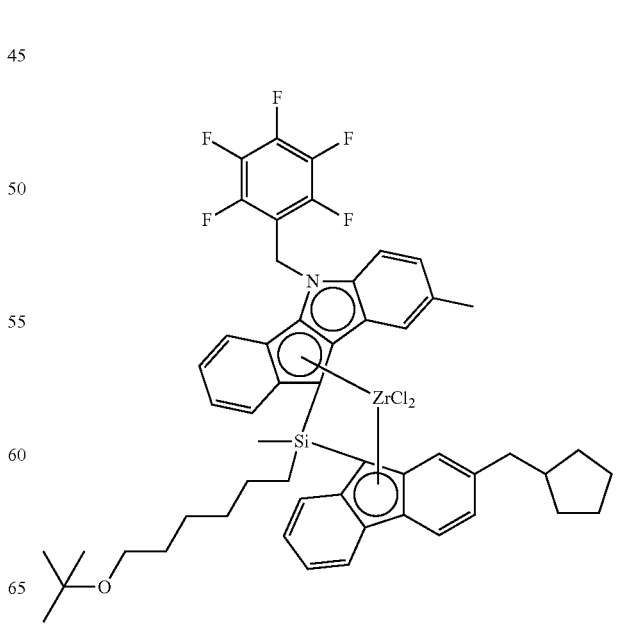

39
-continued
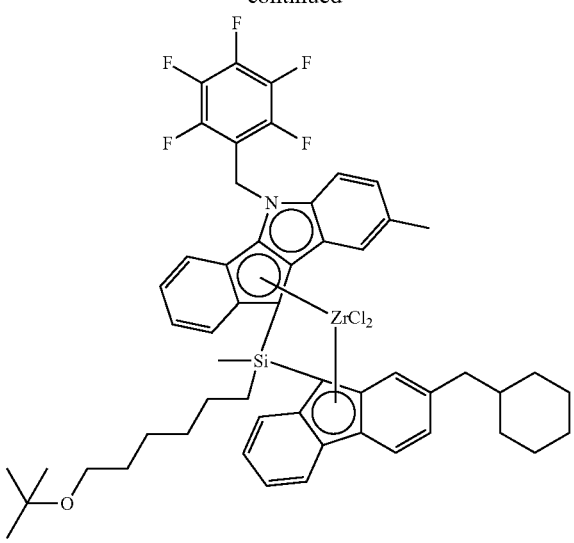
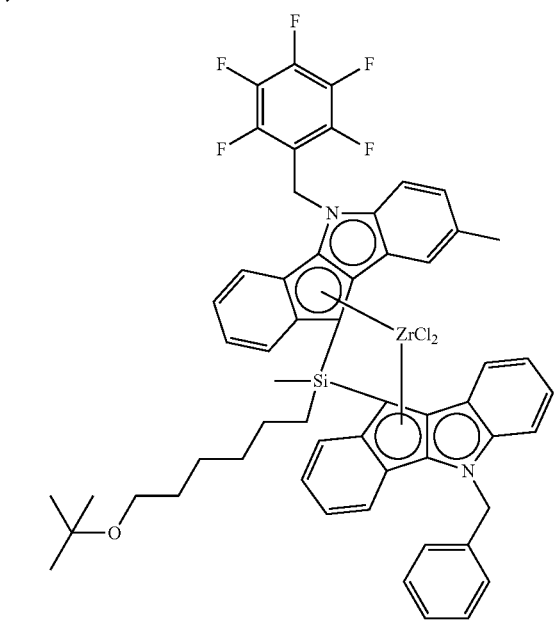
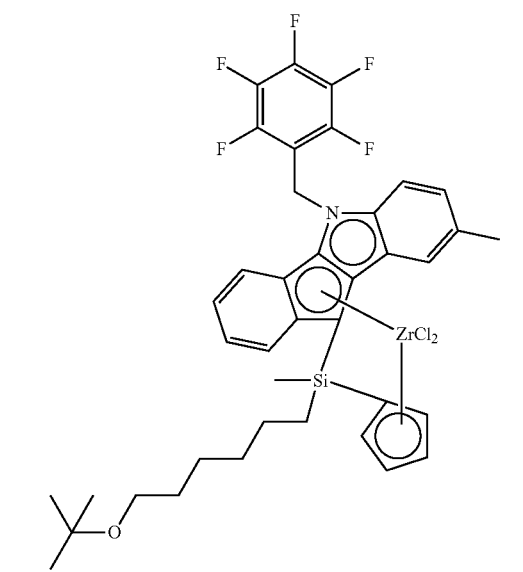
40
-continued
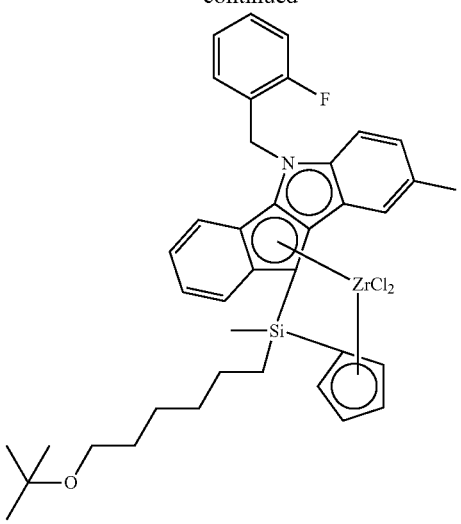
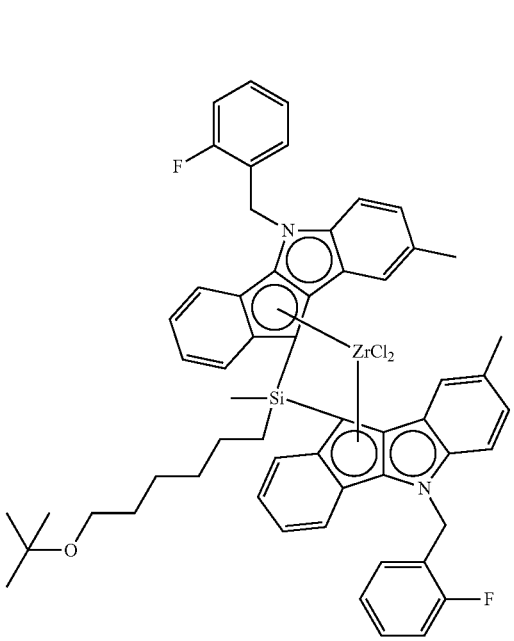
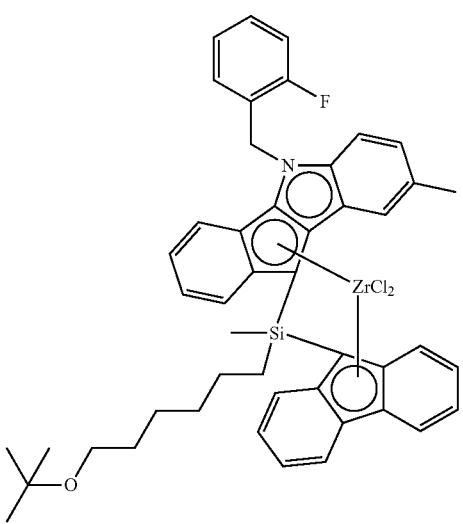

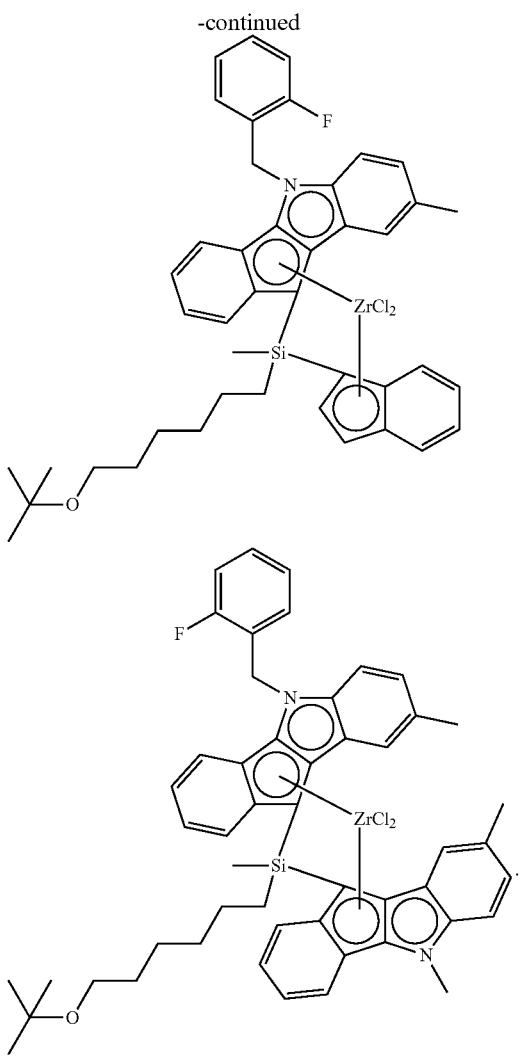

8. A catalyst composition comprising the metallocene compound of claim 1 and a cocatalyst.

9. The catalyst composition of claim 8, wherein the cocatalyst comprises one or more of compounds represented by the following Chemical Formula 3, Chemical Formula 4, and Chemical Formula 5:

$$-[Al(R_{14})-O]_m- \quad \text{[Chemical Formula 3]}$$

wherein, in Chemical Formula 3,
$R_{14}$'s are the same as or different from each other, and are each independently a halogen;
hydrocarbon having 1 to 20 carbon atoms; or halogen-substituted hydrocarbon having 1 to 20 carbon atoms; and
m is an integer of 2 or more, $$J(R_{14})_3 \quad \text{[Chemical Formula 4]}$$

wherein, in Chemical Formula 4,
$R_{14}$'s are the same as defined in Chemical Formula 3; and
J is aluminum or boron, $$[E-H]^+[ZA'_4]^- \text{ or } [E]^+[ZA'_4]^- \quad \text{[Chemical Formula 5]}$$

wherein, in Chemical Formula 5,
E is a neutral or cationic Lewis acid;
H is a hydrogen atom;
Z is a Group 13 element; and
A's are the same as or different from each other, and are each independently an aryl group having 6 to 20 carbon atoms or an alkyl group having 1 to 20 carbon atoms, of which one or more hydrogen atoms are unsubstituted or substituted with a halogen, a hydrocarbon having 1 to 20 carbon atoms, alkoxy, or phenoxy.

10. The catalyst composition of claim 8, wherein the catalyst composition is in the form of being supported on a support.

11. The catalyst composition of claim 10, wherein the support is one or more selected from the group consisting of silica, silica-alumina, and silica-magnesia.

12. A method of preparing an olefin-based polymer, comprising the step of polymerizing olefin-based monomers in the presence of the catalyst composition of claim 8.

13. The method of claim 12, wherein the polymerizing is carried out by a solution polymerization process, a slurry process, or a gas phase process.

14. The method of claim 12, wherein the olefin-based monomer is one or more selected from the group consisting of ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, and 1-eicosene.

* * * * *